United States Patent
Purdy

(10) Patent No.: US 12,310,703 B2
(45) Date of Patent: May 27, 2025

(54) VASCULAR ASSESSMENT USING STATISTICAL ANALYSIS OF RAPID BLOOD PRESSURE READINGS

(71) Applicant: ENDOPHYS HOLDINGS, LLC, Dallas, TX (US)

(72) Inventor: Phillip D. Purdy, Maypearl, TX (US)

(*) Notice: Subject to any disclaimer, the term of this patent is extended or adjusted under 35 U.S.C. 154(b) by 0 days.

(21) Appl. No.: 18/679,234

(22) Filed: May 30, 2024

(65) Prior Publication Data

US 2024/0398244 A1    Dec. 5, 2024

Related U.S. Application Data

(60) Provisional application No. 63/470,409, filed on Jun. 1, 2023.

(51) Int. Cl.
| | |
|---|---|
| *A61B 5/0215* | (2006.01) |
| *A61B 5/00* | (2006.01) |
| *A61B 5/02* | (2006.01) |
| *A61B 5/03* | (2006.01) |

(52) U.S. Cl.
CPC ...... *A61B 5/02154* (2013.01); *A61B 5/02007* (2013.01); *A61B 5/02156* (2013.01); *A61B 5/031* (2013.01); *A61B 5/7225* (2013.01); *A61B 5/7246* (2013.01); *A61B 5/7257* (2013.01); *A61B 2562/0233* (2013.01); *A61B 2562/164* (2013.01)

(58) Field of Classification Search
CPC ............ A61B 5/02154; A61B 5/02007; A61B 5/02156; A61B 5/031; A61B 5/7225; A61B 5/7246; A61B 5/7257; A61B 2562/0233; A61B 2562/164; A61B 5/0215; A61B 5/6852

See application file for complete search history.

(56) References Cited

U.S. PATENT DOCUMENTS

| | | |
|---|---|---|
| 8,273,030 B2 | 9/2012 | Harpas et al. |
| 9,247,909 B2 | 2/2016 | Meyer, Jr. |
| 10,456,046 B2 | 10/2019 | Eagle et al. |
| 10,893,809 B2 | 1/2021 | Denney, Jr. et al. |
| 11,058,308 B2 | 7/2021 | Schmitt et al. |

(Continued)

FOREIGN PATENT DOCUMENTS

| | | |
|---|---|---|
| CA | 2893527 A1 | 7/2011 |
| EP | 0562408 A1 | 9/1993 |
| WO | 2022149106 A1 | 7/2022 |

*Primary Examiner* — Bo Joseph Peng
(74) *Attorney, Agent, or Firm* — James H. Ortega; David W. Carstens; Carstens, Allen & Gourley, LLP

(57) ABSTRACT

A system and method for measuring blood pressure that allows for both coupling of fiber optic pressure sensors with a standard patient care monitor (PCM) and vascular assessment using statistical analysis of pressure wave data. The disclosure has a blood pressure monitor (BPM) system that calibrates and compensates blood pressure data for display on a standard PCM using analog-to-digital-to-analog conversion and Wheatstone Bridge emulation. The BPM can also analyze collected pressure wave data using various statistical methods. Using fast Fourier transform (FFT), pressure wave data can be used in vascular assessments to image or otherwise graphically display key vessel attributes. This permits localized intervention and detection of physiologic attributes of vessels prior to the grossly evident anatomical interruption.

18 Claims, 23 Drawing Sheets

(56) References Cited

U.S. PATENT DOCUMENTS

| | | |
|---|---|---|
| 11,406,271 B2 | 8/2022 | Glawdel et al. |
| 2013/0324814 A1 | 12/2013 | Maarek |
| 2015/0119724 A1* | 4/2015 | Weber .................. A61B 5/0261 |
| | | 600/478 |
| 2016/0073959 A1 | 3/2016 | Eagle et al. |
| 2019/0200884 A1 | 7/2019 | Kuenen et al. |
| 2019/0314575 A1* | 10/2019 | Wilcox ................. A61M 5/172 |
| 2024/0398244 A1* | 12/2024 | Purdy .................... A61B 5/031 |

* cited by examiner

VASCULAR ASSESSMENT USING STATISTICAL ANALYSIS OF RAPID BLOOD PRESSURE READINGS

CROSS-REFERENCE TO RELATED APPLICATIONS

This application claims priority to U.S. Provisional Patent Application No. 63/470,409, filed Jun. 1, 2023, which is incorporated herein by reference in its entirety for all purposes.

This application is related to U.S. patent application Ser. No. 14/553,922, filed on Nov. 25, 2014, which is a continuation of U.S. patent application Ser. No. 13/946,646, filed on Jul. 19, 2013, now U.S. Pat. No. 8,926,520, which claims benefit to U.S. Provisional Patent Application No. 61/673,895, filed Jul. 20, 2012, all of which are incorporated by reference.

This application is related to U.S. patent application Ser. No. 14/554,546, filed on Nov. 26, 2014, which is a continuation of U.S. patent application Ser. No. 14/553,922, filed on Nov. 25, 2014, which claims benefit to U.S. Provisional Patent Application No. 61/673,895, filed Jul. 20, 2012; and also is a continuation of U.S. patent application Ser. No. 13/946,646, filed on Jul. 19, 2013, now U.S. Pat. No. 8,926,520, which claims benefit to U.S. Provisional Patent Application No. 61/673,895, filed Jul. 20, 2012, all of which are incorporated by reference herein in their entireties for all purposes.

This application is related to U.S. patent application Ser. No. 14/335,525, filed on Jul. 18, 2014, which claims benefit to U.S. Provisional Patent Application No. 61/847,847, filed Jul. 18, 2013, both of which are incorporated by reference herein in their entireties for all purposes.

This application is related to U.S. patent application Ser. No. 18/202,388, filed on May 26, 2023, which is a continuation of U.S. patent application Ser. No. 16/825,712, filed on Mar. 20, 2020, now U.S. Pat. No. 11,666,233, which claims benefit to U.S. Provisional Patent Application No. 62/900,256, filed Sep. 13, 2019, all of which are incorporated by reference herein in their entireties for all purposes.

TECHNICAL FIELD

The present disclosure relates to pressure readings. More particularly, and not by way of limitation, the present disclosure is directed to a device, system and method for statistical analysis of pressure readings.

BACKGROUND

In healthcare in humans and others, monitoring of "vital signs" (pulse rate, respirations, blood pressure, temperature, etc.) is done routinely at different intervals. In more invasive procedures (surgical, catheter interventions, etc.), and in intensive care units, vital sign monitoring is performed at increased frequency and the accuracy of such monitoring can have a salutary effect on the outcome of the procedures.

Blood pressure monitoring may be performed using a sphygmomanometer (blood pressure cuff) inflated around an arm or a leg and auscultation is performed during deflation of the cuff to "hear" the pulsations arrive and dissipate during cuff deflation, identifying systolic and diastolic blood pressures, respectively. However, sphygmomanometer observations are performed infrequently—30 seconds or longer inter-observation interval—and are often compromised by external factors (obesity, atherosclerotic changes, environmental noise interfering with pressure auscultation, etc.).

Therefore, in the setting of general anesthesia and more invasive procedures, more frequent and accurate samplings are desirable. In these settings, "invasive" blood pressure monitoring is often performed using a catheter placement inside an artery (most often the radial artery in the wrist) and pressures are obtained by connecting the radial artery catheter, via a fluid-filled section of tubing, to a Wheatstone Bridge transducer. The reference to the foregoing can be found in Phillip Purdy et al., *Use of a pressure sensing sheath: comparison with standard means of blood pressure monitoring in catheterization procedures*, 2017 J. NEUROINTERVENT SURG. 9:766-771 and incorporated herein by reference. The Wheatstone Bridge transducer communicates via cable with standard patient care monitors (PCM) to yield analog tracings of the waveform created within the artery to yield systolic, diastolic, and mean arterial pressures. There are issues related to the Wheatstone Bridge transducer technology, described in the cited article, yielding various degrees of error and potential complications related to placement of the separate radial artery catheter.

Often, in urgent medical settings (stroke, heart attack, hemorrhage, etc.), catheter-based procedures can be performed to treat or otherwise intervene. These procedures most often involve placement of a type of medical device such as a catheter, needle, guidewire, or a sheath in the artery at the beginning of the procedure, and sensors used for the intervention can be placed via that medical device and advanced to the ultimate target organ (brain, heart, etc.). The term "medical device" is defined to include a device that functions, inter alia, to measure a pressure within a blood vessel (artery or vein), bladder, cerebrospinal fluid structure, or other organ in which pressure measurement is desirable, which contains a Fabry-Perot sensor for achieving that pressure measurement. Due to the urgency of these problems, delays related to placement of the separate radial artery catheter (delays of 10-30 minutes or longer) may be undesirable.

In response to this issue, a medical device was developed that incorporates a different type of pressure sensing technology (fiberoptic Fabry-Perot sensor) into the wall of the medical device and digital arterial pressure measurements can be obtained at frequencies of hundreds of observations per second with resolutions of 0.01-0.02 mmHG (millimeters of mercury). This resulted in issuance of patents in the U.S. and elsewhere on both the medical device and the Blood Pressure Monitor (BPM) device to which it is connected.

The Blood Pressure Monitor is connected in many settings to a standard patient care monitor via the patient monitor interface described in Transducer Interface System and method, U.S. Pat. No. 8,926,520 (filed Jun. 19, 2013) (issued Jan. 6, 2015) which is incorporated herein by reference.

The term "blood pressure" refers to the difference measured between the pressure in the atmosphere ("0" pressure) and the pressure generated via the contractions of the heart and transmitted to the arteries. These pressures are read as "systolic" pressure (i.e., the peak pressure of the cardiac cycle) and "diastolic" pressure (i.e., the trough pressure of the cardiac cycle). All patient care monitors measure blood pressure by first "zeroing", which identifies the atmospheric pressure for the monitor. This atmospheric pressure is read as "0" by the patient care monitor and must be input in the beginning of the procedure before the monitor can identify how much higher than atmospheric pressure the pressure in the arteries achieves. All patient care monitors have a "zero" button or switch which, when depressed or otherwise activated, records in the monitor the observed level of pressure in the atmosphere. Performance of a zero calibration is a mandatory function for invasive blood pressure monitoring on patient care monitors.

The use of a Wheatstone Bridge transducer involves the following steps:

Placement of the artery catheter as described above.

Connection of the artery catheter, via fluid-filled tubing, to the Wheatstone Bridge transducer, which has been suspended on a standard IV pole at the approximate level of the patient's heart (one source of error).

A "3-way" stopcock is connected between the fluid-filled tubing and the Wheatstone Bridge.

The stopcock includes a selector valve between 2 inputs and there is one other "way" on the stopcock constituting the output.

One input of the stopcock ("A") connects to the tubing and the other input has no connection (i.e., the arm of the stock opens to room air-"B").

The output of the stopcock connects to the Wheatstone Bridge ("C"). Hence, when the stopcock is open to air, the Wheatstone Bridge "sees" air pressure.

When the stopcock is open to the artery catheter, the Wheatstone Bridge "sees" blood vessel pressure.

"Zeroing" the Wheatstone Bridge to the patient care monitor as follows:

The stopcock has been initially connected to A.

The stopcock is temporarily closed to A and opened to B.

While the stopcock is opened to B, the "zero" button on the patient care monitor is depressed and held depressed until the monitor displays "0".

The monitor is now "zeroed" to room air, and the stopcock is switched back to its B arm communication with the Wheatstone Bridge. The pressures "seen" by the monitor now are the pressures in the artery, and the pressures displayed are the high (systolic) and low (diastolic) pressures in comparison to the remembered "zero" pressure. These pressures are displayed as mmHg (millimeters of mercury).

Since all pressures obtained from the Fabry-Perot sensor ("sensor") in the medical device are obtained from the diaphragm of the sensor, which will be inside the artery as soon as the sheath medical device is inserted, the sensor must be "zeroed" prior to insertion in the artery. This is currently done via connection of the sensor output to the blood pressure monitor (BPM) prior to sensor insertion into the artery, and the Zero value is obtained within the BPM and while the sensor is not in the artery, the "Zero" button on the patient care monitor is depressed, per step C above. The zero-calibration value from the sensor can then be stored in the BPM, and if, for some reason, the sensor (medical device) is disconnected from the BPM, upon reconnection to the BPM the BPM identifies the sensor and collects the zero calibration from its memory. When the PCM has not been "re-zeroed" or disconnected from the BPM during the interruption, the remembered zero allows the BPM to communicate pressures accurately to the patient care monitor. A failure to properly "zero" and account for atmospheric pressure will lead to incorrect pressure measurements and possibly incorrect medical care as a result.

It would be advantageous to have a device, system and method for statistical analysis of pressure readings that overcomes the disadvantages of the prior art. The present disclosure provides such a device, system and method.

BRIEF SUMMARY

The present disclosure generally comprises an optical sensor placed in a housing having a deformable membrane, wherein the light reflects off of the membrane, a signal conditioner that processes the reflected light into an electrical signal proportional to the amount of deformation of the membrane caused by pressure in the vessel, and a blood pressure monitoring system which performs an analog-to-digital-to-analog conversion process in which an analog sensor input is converted to digital and then compensated using calibration factors. The results of this compensated digital data are then converted to analog and presented to a Wheatstone Bridge emulator that receives excitation input from an external patient care monitor (PCM) or other stimulus systems. The excitation input from the PCM is used as a reference voltage to modulate the analog sensor data to emulate the characteristics of a conventional Wheatstone Bridge, resulting in a transparent presentation of the converted analog sensor data to the PCM for analysis/display. The computing device also comprises a system and method for adjusting a pressure reading in accordance with atmospheric pressure and gauge factors specific to the medical device sensor. The gauge factors are stored in a non-volatile memory. When the analog pressure sensor takes an observation of the patient's internal blood pressure, the observation is combined with the zero value to produce a compensated pressure value. In addition to calibrating and compensating sensor data, the computing device can be used to apply various statistical analyses to pressure wave data.

The analog-to-digital-to-analog conversion process permits high-performance sensors to be attached to conventional PCM system hardware without the need for any PCM modifications. High-performance sensors can more accurately measure internal blood pressure and collect additional pressure wave data. Using statistical analysis, the computing device can analyze pressure wave data to determine vessel attributes. Additionally, individual analog sensor calibration factors ensure that the analog sensors need not be trimmed or compensated for by the PCM to ensure accurate measured sensor results. Both analog and digital outputs from the BPM are communicated to the PCM and to a separate external computing device via a separate output (USB port, etc.). This enables the PCM to display pressures as if they were coming from a Wheatstone Bridge, while the USB port transmits individual pressure readings with higher resolution, and frequency transmission of digital data may occur via other means not part of the current embodiments (i.e., Bluetooth wireless transmission, etc.).

The present disclosure may be utilized in the context of an overall blood pressure analysis method, wherein the blood pressure analysis system described previously operates in conjunction with application software read from a computer-readable medium that executes on a variety of computerized hardware that includes but is not limited to microcontrollers, personal computers, laptops, tablet computers, cellphones, smartphones, etc. Other aspects, embodiments and features of the present disclosure will become apparent from the following detailed description when considered in conjunction with the accompanying figures. In the figures, each identical, or substantially similar component that is illustrated in various figures is represented by a single numeral or notation. For purposes of clarity, not every component is labeled in every figure. Nor is every component of the disclosure shown where illustration is not necessary to allow those of ordinary skill in the art to understand the disclosure.

BRIEF DESCRIPTION OF THE DRAWINGS

The novel features believed characteristic of the disclosure are set forth in the appended claims. The disclosure itself, however, as well as a preferred mode of use, further objectives and advantages thereof, will be best understood by reference to the following detailed description of illustrative embodiments when read in conjunction with the accompanying drawings, wherein:

DETAILED DESCRIPTION

Embodiments of the disclosure will now be described. The device measures fluid pressure and maps the internal surface of a vessel carrying fluid using a fiberoptic sensor and statistical methods to transform collected data. In at least one example, the device creates compatibility between fiber optic sensors and a common physiological patient care monitor (PCM). The device also provides expanded functionality for enhanced applications such as real-time analysis of internal blood pressure waveforms, dynamic control of data acquisition and display, and utilization of statistical analysis to determine key vessel attributes.

Fiber optic pressure sensors are extremely accurate and, when placed in an arterial blood vessel, provide significantly better real-time blood pressure information to a clinician compared to a Wheatstone Bridge transducer. Specifically, medical personnel such as cardiologists, vascular surgeons, anesthesiologists, neurosurgeons, interventional radiologists, trauma physicians, emergency medical technicians, etc., all need accurate real-time indications of a patient's arterial blood pressure during critical care situations. Fiber optic sensors are also immune to the effects of electromagnetic radiation. They can be used in intense radiological imaging environments without degradation, thus providing the ability to provide superior real-time measurements in many clinical settings. Fiber optic pressure sensors are also capable of collecting additional pressure waveform data compared to other blood pressure sensing devices, which can be particularly useful for clinicians for localized intervention and early detection of physiologic attributes of vessels.

The disclosure accurately emulates a fluidic invasive arterial blood pressure transducer and supplies electrical signals to its output that are indistinguishable from a conventional fluidic blood pressure sensor or in some examples a Wheatstone Bridge emulation. It also supports modern computer communications interfaces, analog/digital human interface status indicators, and collection and statistical analysis of detailed pressure wave data. The disclosure can be designed to be used primarily in surgical procedures and critical patient care situations where the accuracy and timeliness of IBP systolic and diastolic measurements are very important. Other versions of the disclosure can be redesigned to be able to enable localized intervention and detection of physiologic attributes of vessels prior to the grossly evident anatomical interruption. The present disclosure explicitly supports disposable fiber optic sensors that may be incorporated into other medical devices, such as catheters and sheaths.

Figure 1:
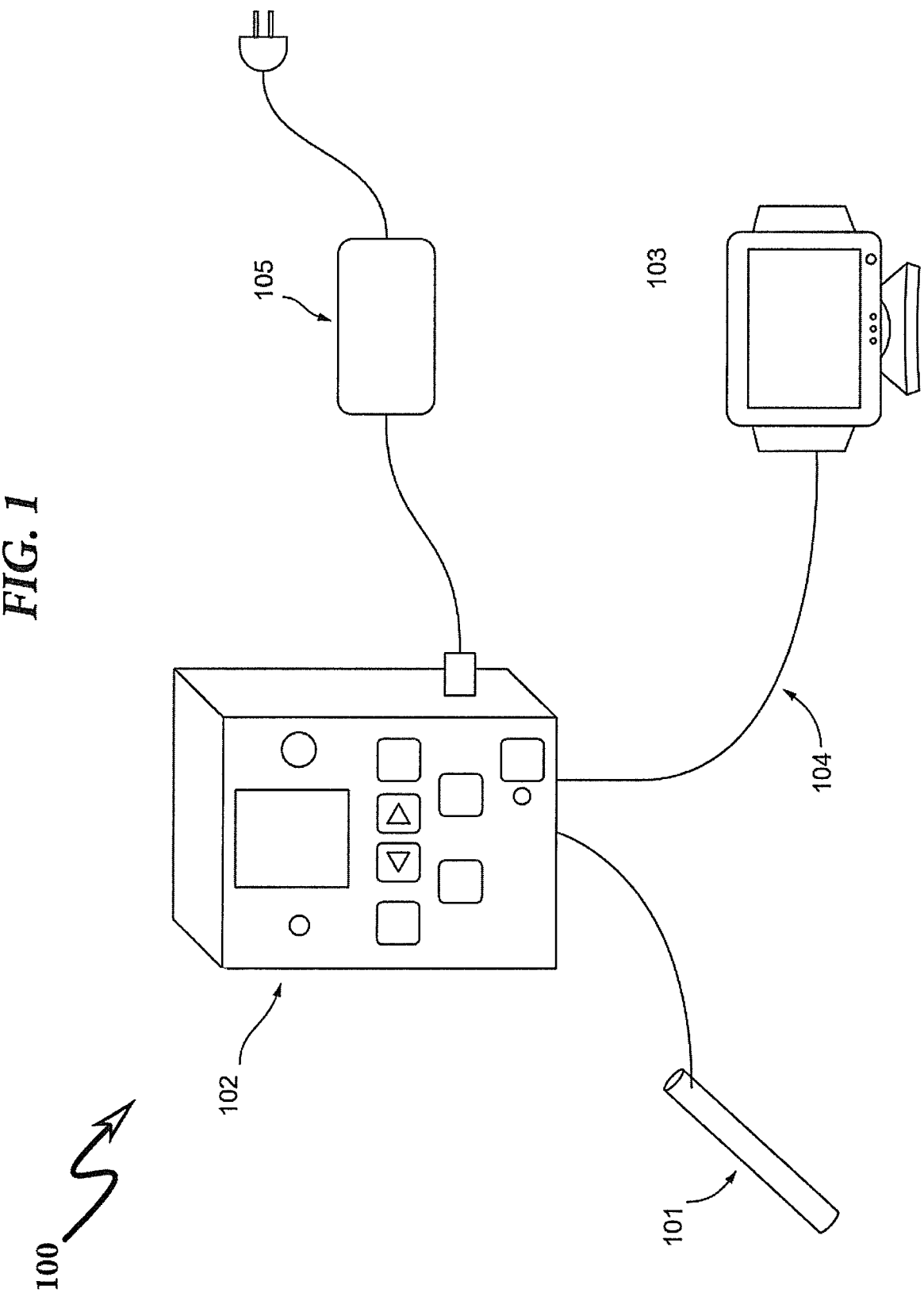
FIG. 1 illustrates a perspective view of the device.

FIG. 1 is a perspective view of the device 100. In one example, the pressure sensing sheath system 101 contains a fiber optic sensor and a signal conditioner. In another example, the signal conditioner is a component separate from the pressure sensing sheath system. A fiber optic sensor detects fluid pressure within a vessel. Output from a fiber optic sensor is received by a signal conditioner. Output from a signal conditioner is received by a blood pressure monitor (BPM) system 102, In another example, the signal conditioner is part of the BPM 102. A BPM 102 is connected to a power module 105 and coupled to a PCM 103 via an adapter cable 104. A BPM 102 integrates the output from a signal conditioner with the output from a PCM 103 originally designed to interface with an external pressure transducer. Using these outputs, the BPM 102 generates an output to the PCM 103. The output from a BPM 102 is an accurate replication of the input that would be received by a PCM 103 from a Wheatstone Bridge external pressure transducer. The BPM 102 automatically reads, identifies, and configures itself to adapt to the unique characteristics of each fiber optic sensor and provides an indication of the integrity of the sensor readiness. It senses internal system status and activates indicators that track its condition.

Figure 2:
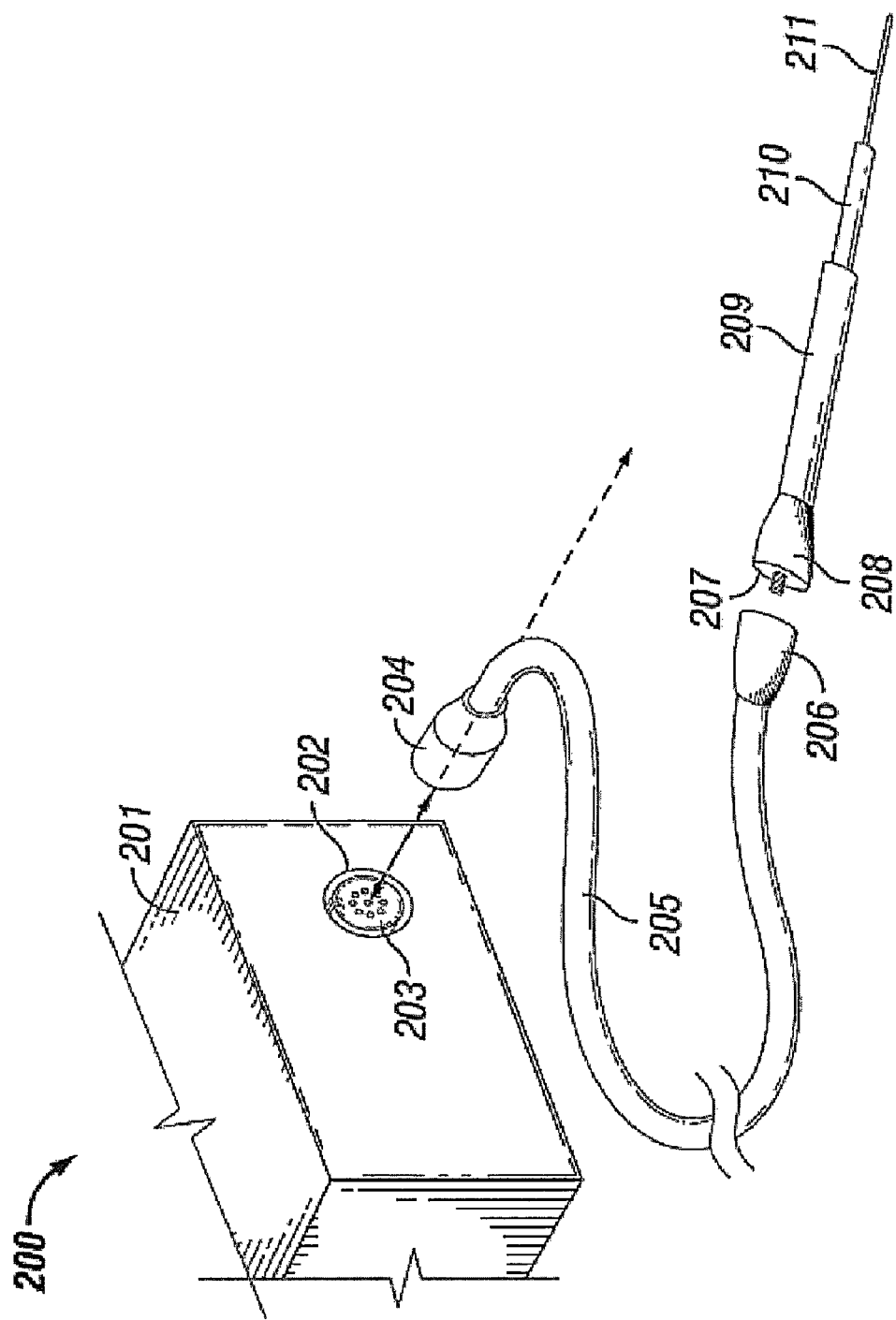
FIG. 2 is a perspective view of one example of the device.

FIG. 2 illustrates a perspective view of one example of the device 200. The disclosure includes a medical device 210 for inserting into a patient that is coupled to a BPM 201 through a male connector 207 to a female cable connector 206, a cable 205, a male cable connector 204, and then to a female coupling device 203 that is inside of a port 202 which is affixed to the BPM 201. In at least one example, the cable 205 is a fiber optic cable. The medical device 210 can be adapted to be coupled to the BPM 201 through other types of cables, likely depending on the type of sensor 211 used in the device. In another example, data may be transmitted wirelessly (e.g., via Bluetooth) from a sensor to the BPM or a remote location for analysis.

The medical device 210 contains the fiber optic sensor apparatus, made up of a sensor 211, a signal conditioner, and a measurement device for providing information regarding the location of the medical device 210 within the vessel. Localization of the medical device 210 can also be obtained via imaging methods such as fluoroscopy or ultrasonography. Sensor 211 is located at the tip of the medical device 210. The sensor 211 may be a Fabry-Perot pressure sensor or another type of fiber optic sensor. The medical device 210 is connected to catheter tubing 209, which is connected to a sensor connector 208 that utilizes a male connector 207 to interface with cable 205 through the female cable connector 206.

While the medical device 210 is intended to be inserted into the vasculature of a patient such that the current blood pressure and vessel attributes can be observed in situ, the device can be configured to allow for the medical device 210 to be situated outside the patient. For example, the medical device could be located outside the patient level with the patient's heart and connected to a patient through a catheter that has an end inserted inside the patient such that the analog sensor can detect the blood pressure waves inside the patent by being in fluidic contact with the vasculature of the patient. Additionally, the disclosure may also be used to measure pressures for fluids other than blood pressure.

Once the medical device 210 is inserted into the patient, the sensor 211 is not required to be recalibrated in accordance with a current atmospheric pressure reading in order for an accurate blood pressure observation from the patient to be obtained. Instead, the BPM 201 initiates a zero function in order to obtain a current observation of atmospheric pressure. The zero function is initiated when the BPM 201 detects that it has been coupled with a medical device 210. The zero function is performed by the BPM 201 by observing and recording the current atmospheric pressure. In order to derive a zero factor, the observation of atmospheric pressure is utilized with the gauge factors that are specific to the BPM 201, along with gauge factors that are specific to a sensor 211 retrieved from being stored in non-volatile memory. While many different forms of non-volatile memory may be used in conjunction with the BPM, EEPROM memory and RFID TAG memory are currently considered optimal. It is also preferable that a pre-existing zero factor be erased and replaced with the newly derived zero factors each time the zero function is initiated. The zero function can be initiated by a user by decoupling the medical device 210 from the BPM 201 and then recoupling it.

Figure 3:
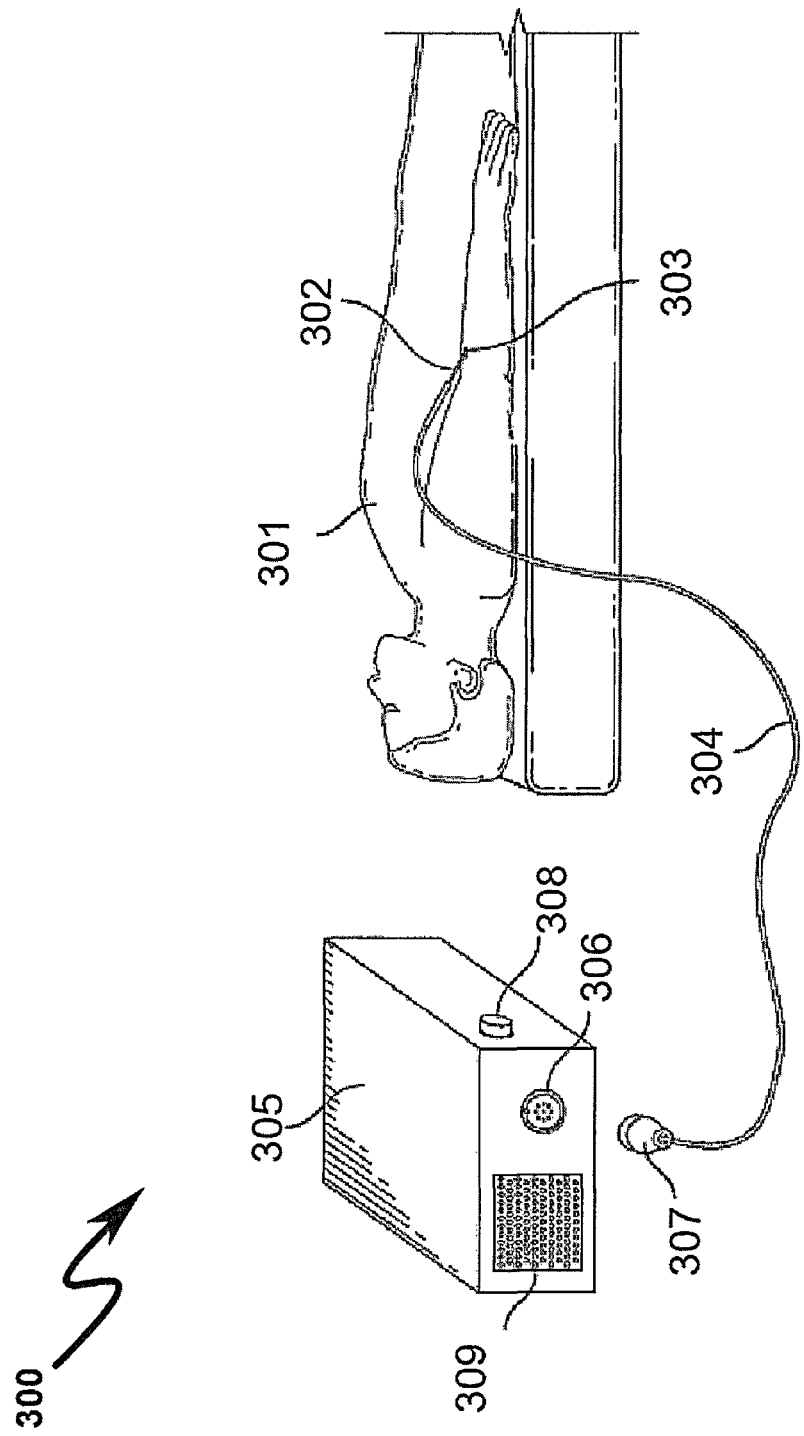
FIG. 3 is an environmental view of the device utilized in a patient.
Figure 4:
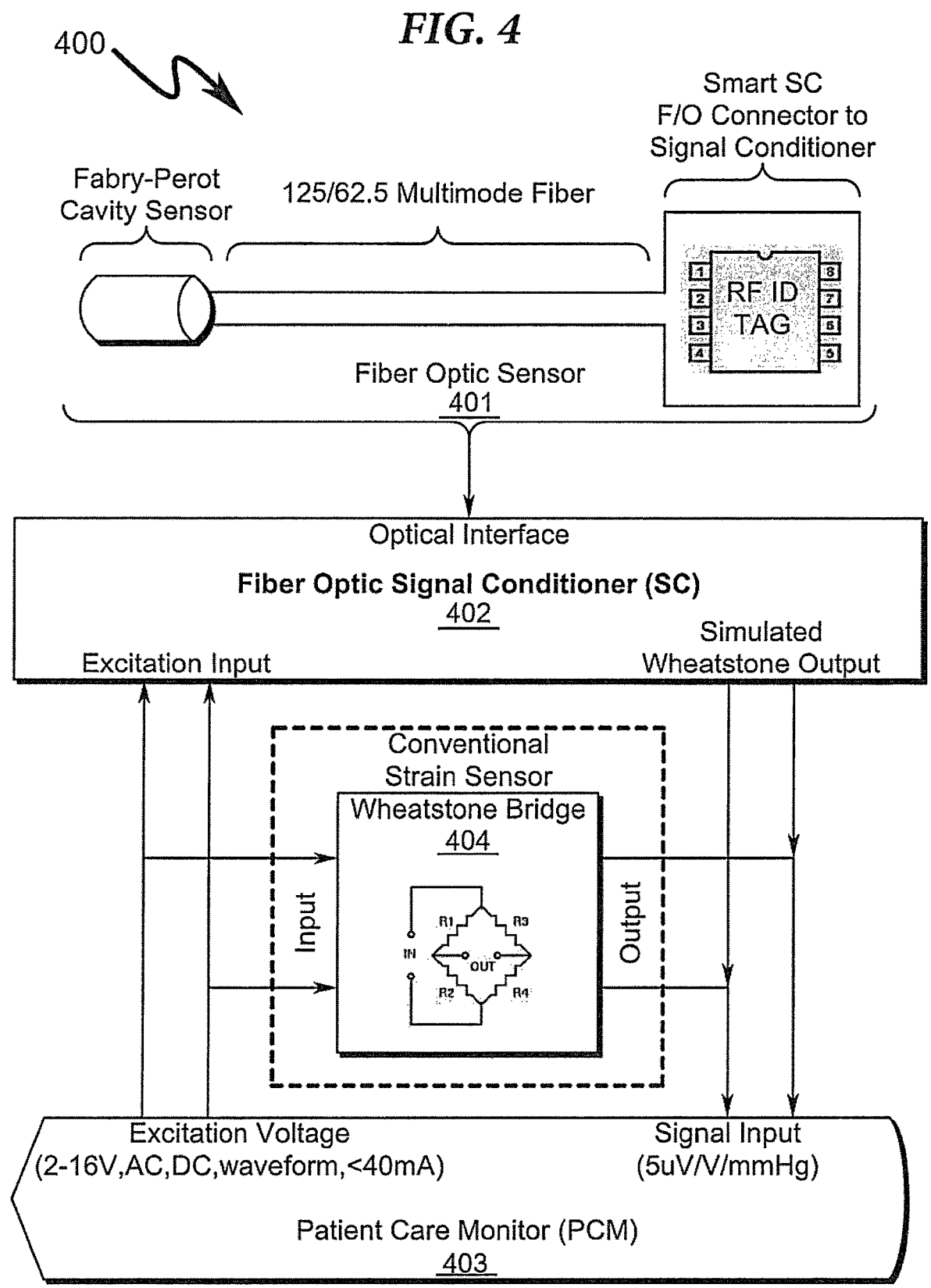
FIG. 4 illustrates the basic components of a conventional fiber optic fluidic pressure transducer.

FIG. 3 illustrates an environmental view 300 of the BPM 305 utilized in a patient 301. The medical device 302 has been inserted into a patient 301 at a point in the patient's body 303. The specific point 303 at which the medical device 302 is located in the patient 301 depends on where the user intends to measure the patient's blood pressure. The medical device 302 is coupled through a cable 304 with a connector 307 into the BPM 305 through a port 306. FIG. 4 further illustrates that the grate 309 may be located anywhere on the outside of the BPM 305, or maybe normal ventilation pathways such as small spaces (i.e., not air-tight) around switches, etc., just as long as it allows for the BPM sensor inside to be exposed to atmospheric pressure. Also included in FIG. 3 is the zero switch 308, which allows for the BPM 305 to initiate a zero function without decoupling and recoupling the sheath with the BPM 305.

FIG. 4 illustrates the basic components of a conventional fiber optic fluidic pressure transducer 400. The fiber optic pressure sensor assembly 401 consists primarily of three parts. The Fabry-Perot pressure-sensitive diaphragm can be mounted at the distal end of a cavity which is the sensor itself. Pressure-induced deflections of this diaphragm modulate light shining on it and reflect the light down the fiber optic cable, which is the second part. The third part is a fiber optic connector that connects to a signal conditioner 402 and contains a non-volatile memory holding sensor, transducer-specific gauge factors, an atmospheric correction factor, and/or other relevant information.

The signal conditioner 402, which can be independent, is a part of the sensor or part of the BPM, which may be defined as an electro-optical unit that controls, processes, and converts the pressure modulated light signal from the fiber optic sensor into electrical signals for subsequent interpretation and/or retention and display. The signal conditioner 402 excites a fiber optic Fabry-Perot pressure sensor and processes the reflected light into an electrical signal proportional to the physiological pressure on the sensor 401. The optical interferometer combines the excitation light and the reflected signal light to produce an optically modulated signal that indicates the pressure-induced deformation of the Fabry-Perot sensor cavity. This optically modulated signal is detected using photodetectors (or alternatively detected by a CCD imaging array) and converted to an electrical signal that is stored in a digital memory used for subsequent processing. The microprocessor processes the digital pressure data and converts it to a format compatible with a serial digital output and/or supplies the data to a digital-to-analog (D/A) converter that produces an analog signal output. A power electronics subsystem (not shown) converts a single power input into multiple voltages needed by the various components in the signal conditioner 402.

FIG. 4 also illustrates a conventional internal blood pressure PCM 403 and a Wheatstone Bridge resistive pressure sensor 404. The bridge is excited by a voltage from the PCM 403. The sensor elements change their resistances based on the strain (pressure) on them. These changes in the resistance values unbalance the bridge and produce a voltage proportional to the excitation voltage and the pressure. The fiber optic signal conditioner 402 substitutes the fiber optic sensor 401 for the conventional strain sensor 404 used by the PCM 403.

Figure 5:
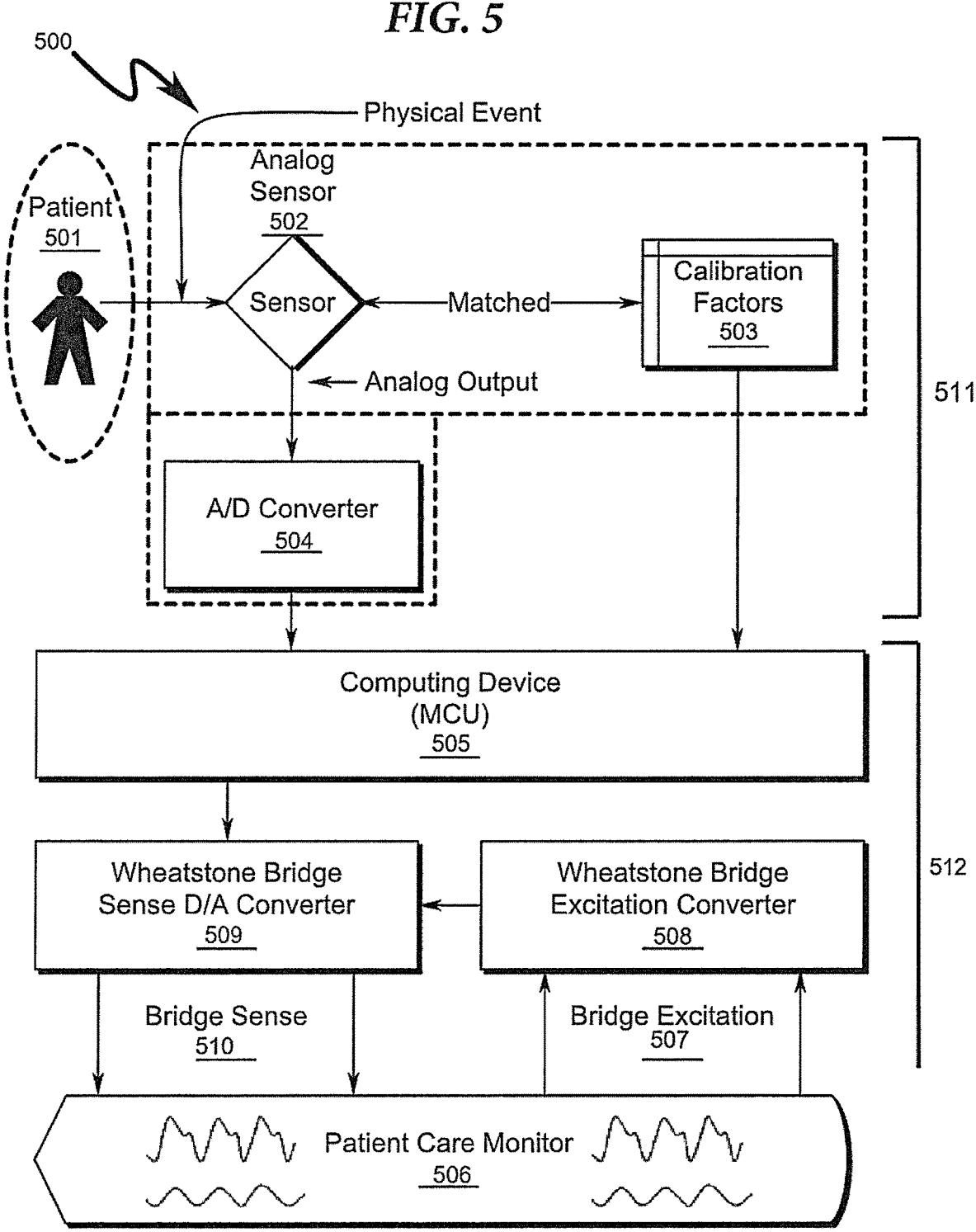
FIG. 5 illustrates a system block diagram of one example of the device as applied to an analog patient status sensor monitored by a patient care monitor (PCM)

FIG. 5 illustrates at least one example of the device 500, in which the device may be implemented as a self-contained unit comprised of a fiber optic sensor apparatus 511 as an input source, a BPM 512 interface, and a PCM 506 as an output. In at least one example, the system is applied to a collection of data associated with a patient in a healthcare application context. Within this context, the patient 501 is monitored by an analog sensor 502 that has associated with it calibration factors 503 that describe a conversion from the analog values produced by the sensor 502 to a normalized set of standardized values. For example, a fiber optic pressure sensor might incorporate calibration factors converting measured optical transit delays (or other measured physical data associated with the optical sensor) to absolute pressure values.

The fiber optic sensor apparatus 502 analog output is converted to digital by an analog-to-digital (A/D) converter 504. This analog sensor A/D converter data is presented to a computing device 505 within a BPM 512, along with the calibration factors 503. The computing device integrates the analog sensor A/D converter data with the calibration factors 503. Raw sensor 502 information is compensated by the calibration factors 503 to produce data that may be interpolated if necessary to produce sensor information that is accurate over a wide dynamic range of sensor inputs.

Since the design of current patient care monitors presumes connection to a Wheatstone Bridge sensor, a BPM 512 also contains a Wheatstone Bridge emulator that automatically applies corrections to the absolute fiber optic pressure sensor apparatus 511 signal to scale it to the appropriate values needed by the specific PCM 506. The analog sensor A/D converter data and the calibration factor data are combined by the computing device 505 to produce a digital sensor compensated value. The digital sensor compensated value is converted by a D/A converter 509. This D/A converter data is combined with analog excitation signaling 507 generated by a PCM 506 that has been converted by a Wheatstone Bridge Excitation Converter 508. Converted PCM excitation signaling is used as a scaling reference for the Wheatstone Bridge emulator. Combined D/A converter data and Wheatstone Bridge Excitation Converter 508 signaling is subsequently presented to the PCM 506 as a compensated analog bridge sense signal 510. This compensated analog bridge sense signal 510 represents a fully compensated and calibrated conversion of the analog sensor 502 output that is scaled in proper form for processing and display by the PCM 506.

The BPM 512 essentially acts to directly emulate the electrical interface characteristics of conventional fluidic pressure transducers (that common PCMs are compatible with) while providing much more accurate blood pressure data derived from a fiber optic sensor. Electrically emulating a conventional fluidic transducer uniquely allows a fiber optic pressure sensor to be used with a wide variety of existing PCMs without modification of those monitors.

Outputs of the fiber optic signal conditioner are connected to the BPM 512 electronically, including both digital and analog connections. While both commands and pressure data travel over the digital connection, only pressure information is present on the analog connection. If needed, this analog signal may be converted to a digital signal by an A/D converter and stored in random access memory (RAM) by the microprocessor for subsequent processing. The digital communications interface block converts the data using the appropriate communications protocol, and the data is stored in RAM memory.

The computing device 505 is the central processing element in the system and provides the ability to support many other functions than just processing blood pressure data. The computing device 505 executes instructions stored in the firmware EEPROM that manage and process functions such as diagnostics, error handling, normal operation, alarms, etc. The input communications interface sends control commands to the fiber optic signal conditioner as directed by the computing device 505. The computing device 505 controls the function of emulating a conventional non-fiber optic pressure sensor. This is accomplished through continuously reading the particular internal blood pressure excitation voltage present at the PCM 506, and conditioning the pressure data to be proportional to it as the monitor expects. The computing device 505 processes the data stream and sends it to a D/A converter 509, after which it is scaled to the appropriate values for direct output to the PCM 506. During this conversion, the computing device 505 applies a previously selected sensitivity factor (typically, either 5-microvolts/volt/mmHg or 40-microvolts/volt/mmHg)) appropriate to the PCM 506 that is connected to the interface monitor output. This emulation ability provides compatibility with conventional PCMs.

The firmware EEPROM is externally accessible through a second digital communications interface by other computer applications for updating the firmware. This second digital communications interface supports multiple communications protocols. The microprocessor also manages the human interface devices local to the interface. These devices may comprise switches, visual and/or aural indicators, and/or an alphanumeric blood pressure display.

Figure 6:
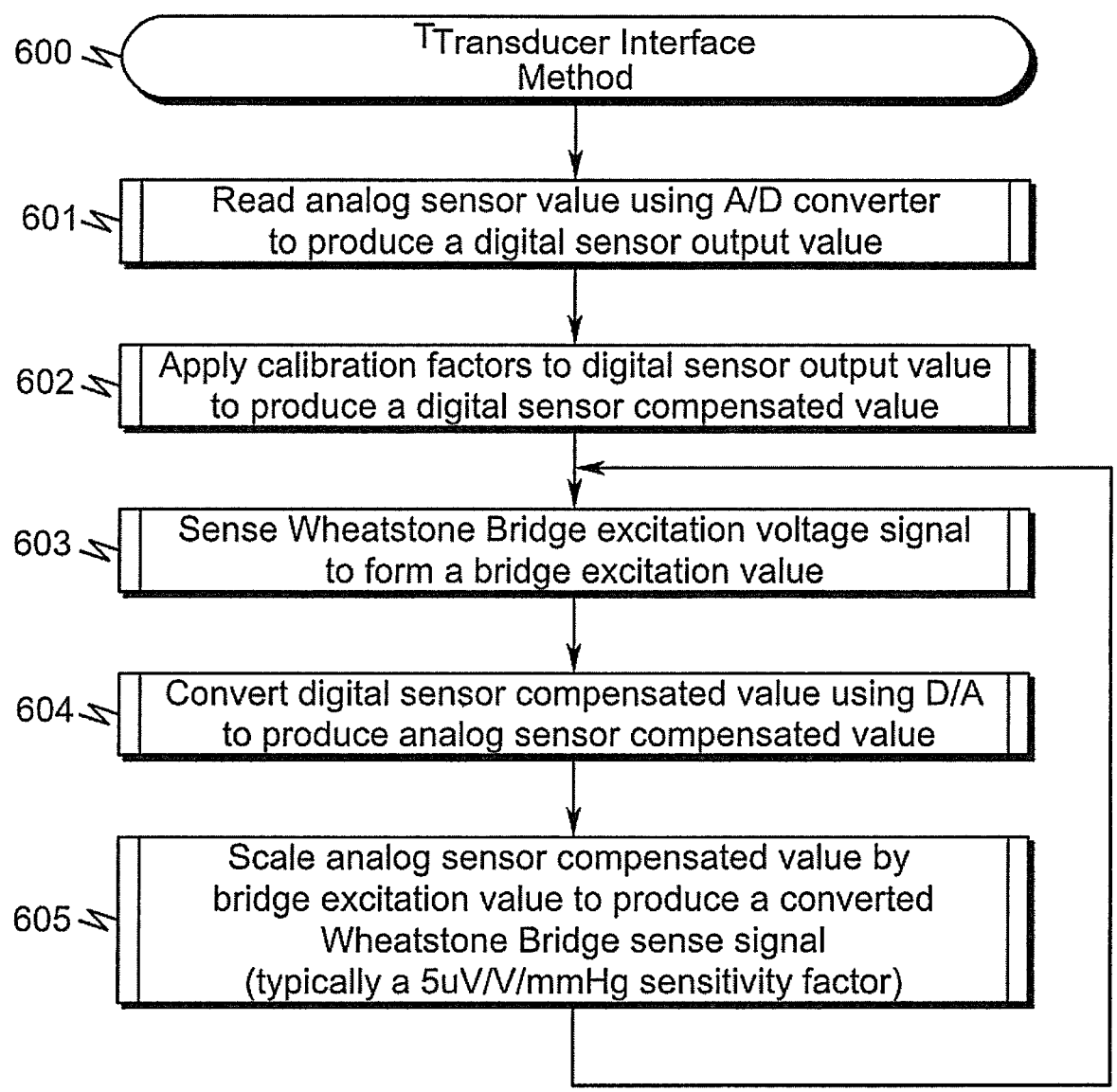
FIG. 6 illustrates a method flowchart of the device method as applied to an analog patient status sensor monitored by a patient care monitor (PCM)

FIG. 6 illustrates a flowchart of the method by which a device produces fully compensated and calibrated conversion of the analog sensor output that is scaled in proper form for processing and display by the PCM sensor data. First, output from an analog sensor output is converted to a digital sensor output value using an A/D converter (Step 601). Calibration factors are applied to digital sensor output values to produce a digital sensor compensated value (Step 602). Next, the device senses a Wheatstone Bridge excitation voltage signal from a PCM to form a bridge excitation reference voltage (Step 603). The digital sensor compensated value is converted to analog using a D/A converter to produce an analog sensor compensated value (Step 604). Finally, the analog sensor compensated value is scaled using the bridge excitation value to produce a converted Wheatstone Bridge sense signal (Step 605).

Figure 7:
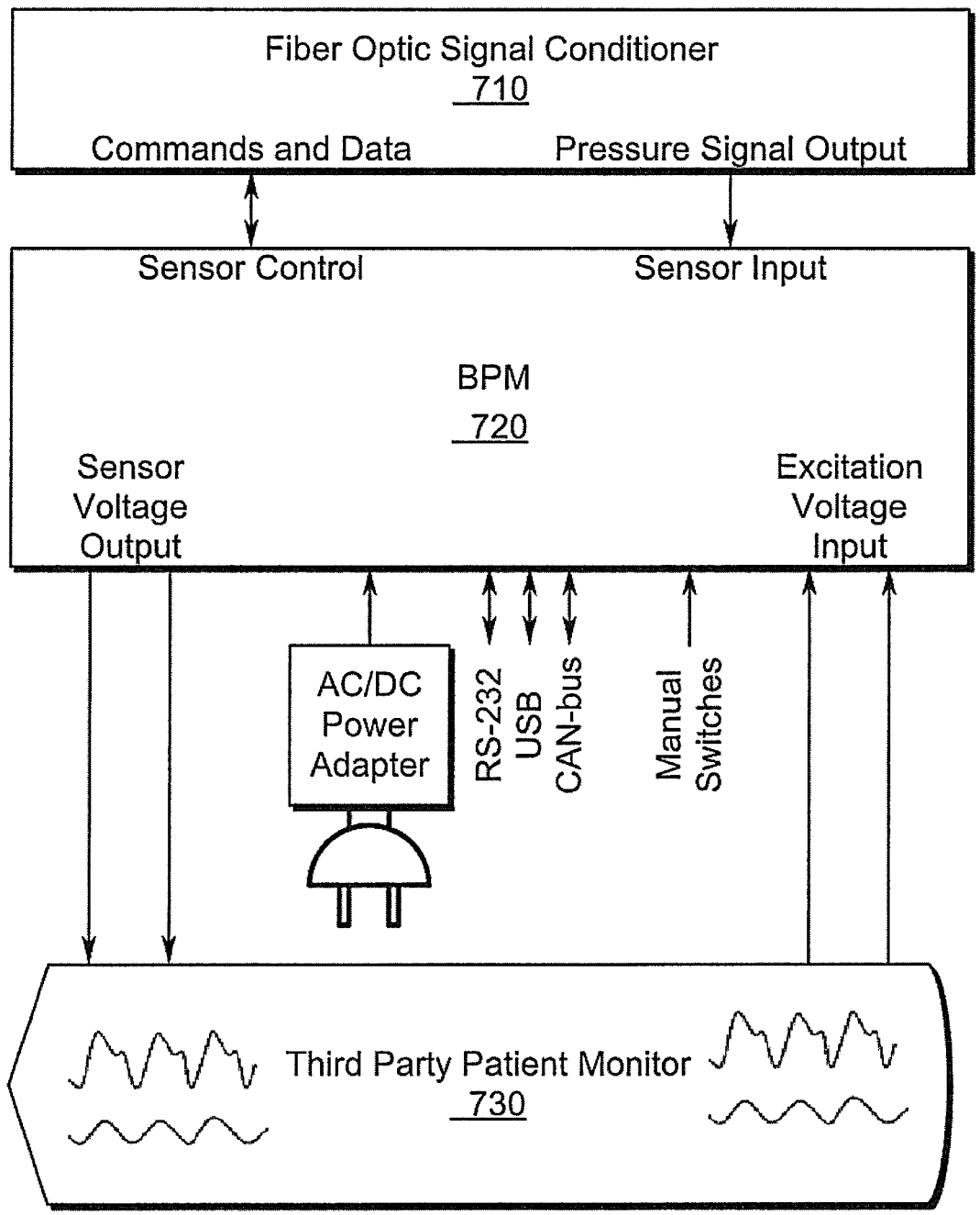
FIG. 7 illustrates an example of the device.

FIG. 7 illustrates an application of the device to a PCM 730. In at least one example 700, a fiber optic signal conditioner 710 interfaces with a fiber optic pressure sensor to generate output signaling based on measured pressure in response to commands and/or data received from a BPM 720. The BPM 720 acts as the "bridge" between the fiber optic pressure sensor and a PCM 730 configured to accept Wheatstone Bridge compatible pressure sensors. Within this context, excitation voltages generated by the PCM 730 are used by the BPM 720 to scale/reference the sensor voltage outputs used to drive the Wheatstone Bridge inputs of the PCM 730.

Figure 8:
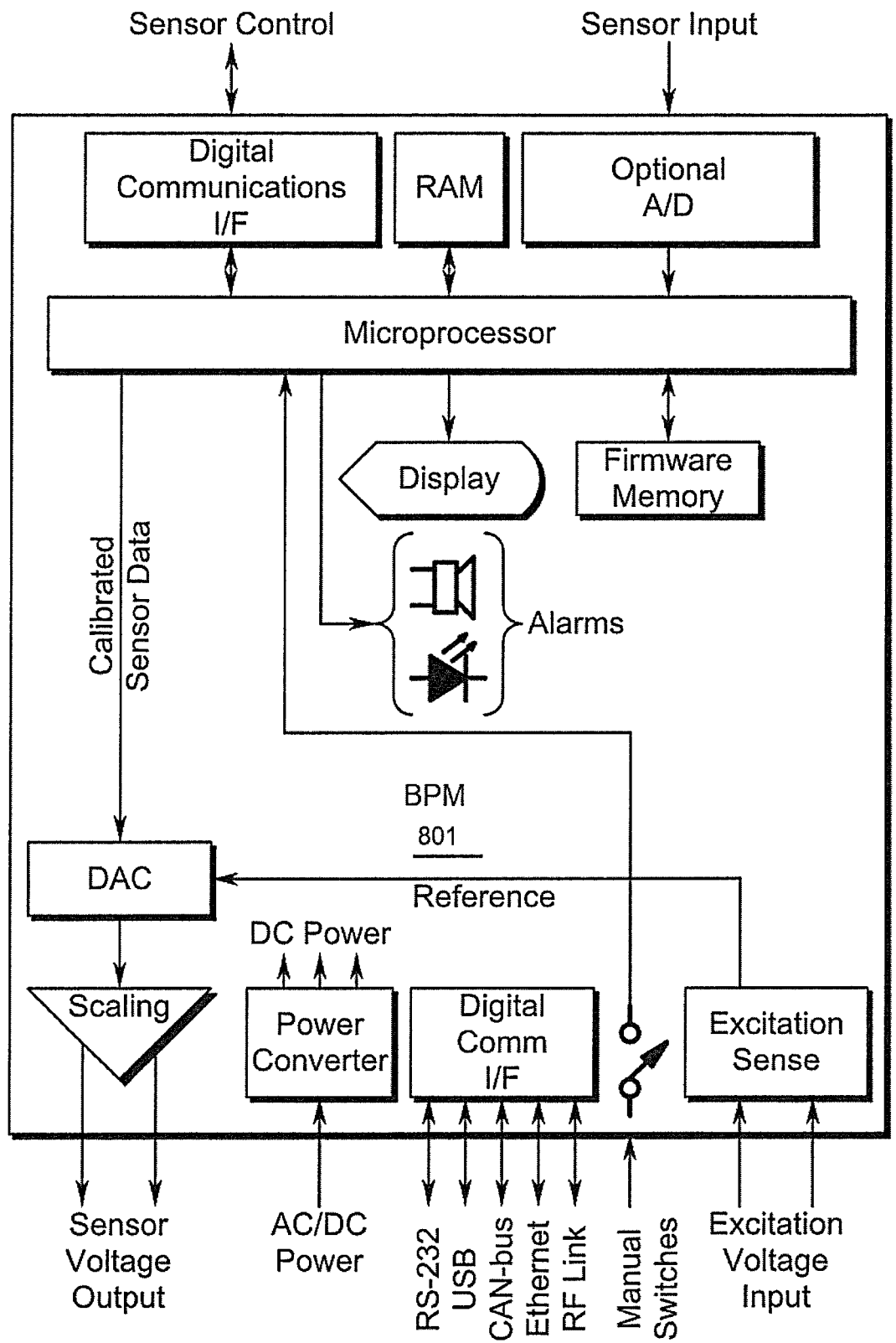
FIG. 8 illustrates an example of the device detailing the internals of a blood pressure monitor (BPM) system.
Figure 9:
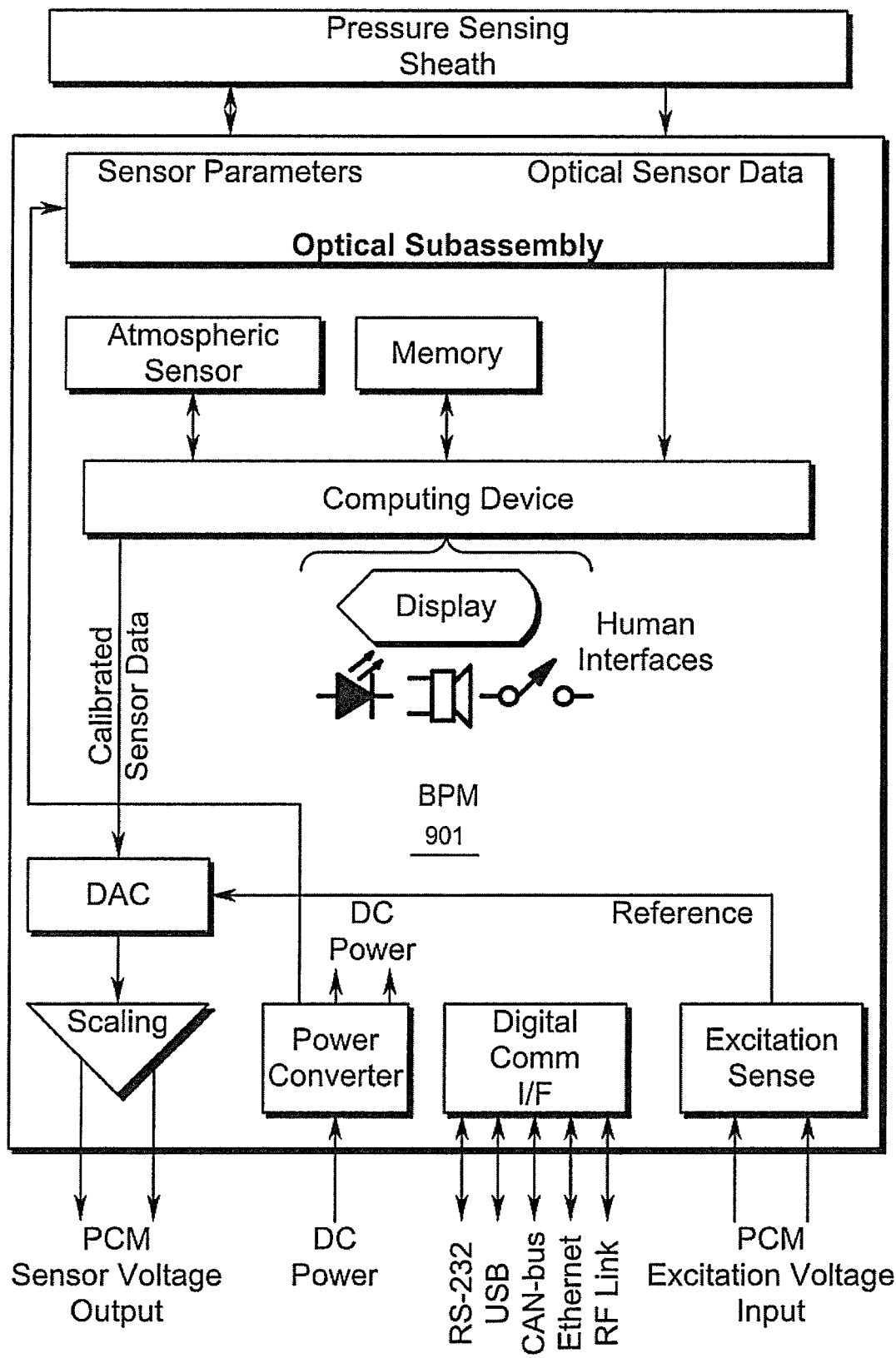
FIG. 9 illustrates an example of the device detailing the internals of a blood pressure monitor (BPM) system.

FIG. 8 and FIG. 9 illustrate examples (800 and 900, respectively) of the BPM 801, 901, respectively, in more detail. The internals of the BPM 801, 901 generally comprise a computing device, RAM, digital communications interfaces, optional A/D converter, display, firmware program memory, human interface alarms, excitation sensing and sensor output voltage generation circuitry, as well as power conversion circuitry and provisions for digital communication to other processors.

Figure 10:
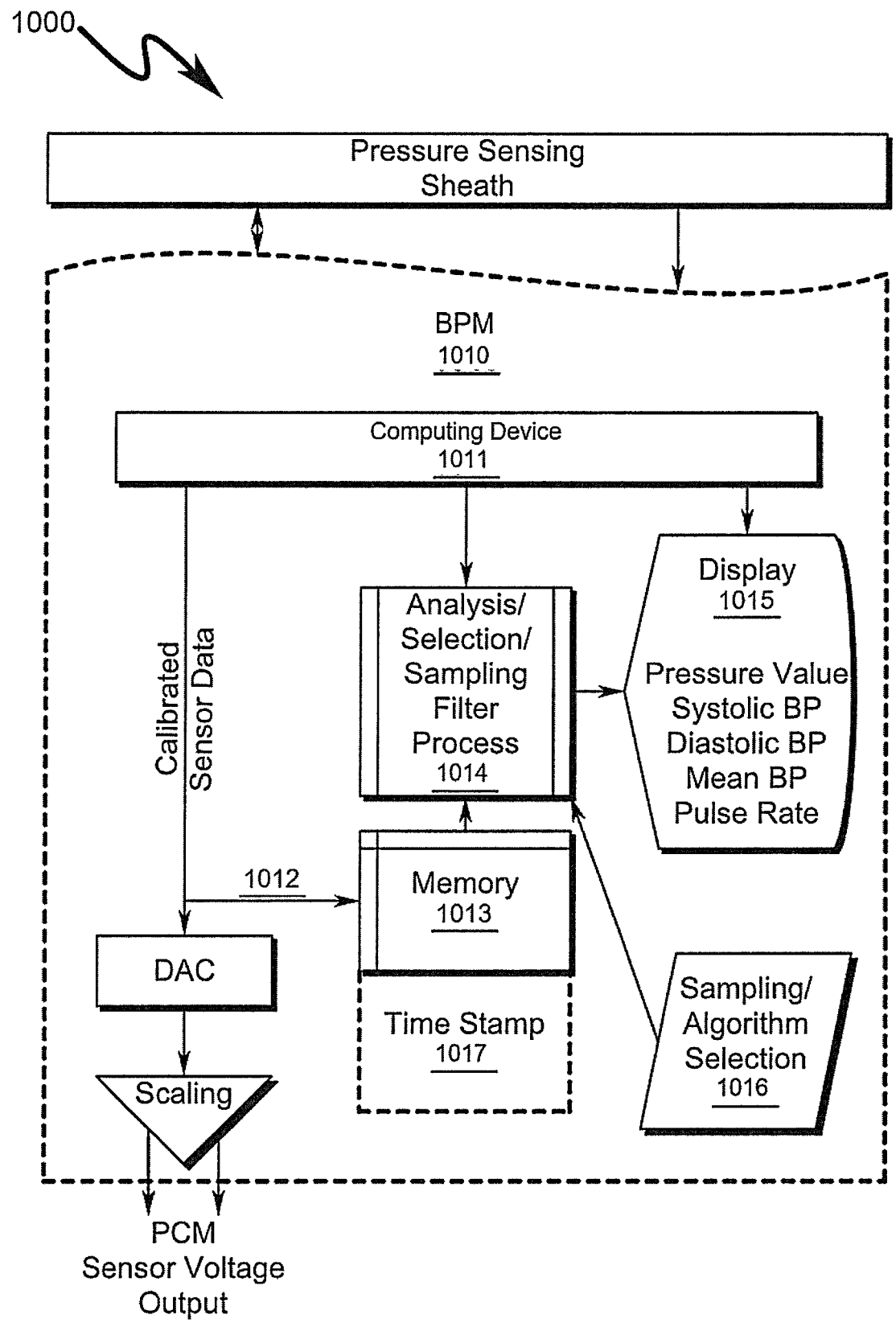
FIG. 10 illustrates an example of the device with a blood pressure monitor (BPM) system configured to display systolic blood pressure, diastolic blood pressure, mean blood pressure, and heart rate values; implementing memory storage of pressure data and selection of this pressure data for presentation on a display; implementing memory storage of pressure data and analysis of this pressure data for presentation on a display; implementing memory storage of pressure data and sampling of this pressure data for presentation on a display.

FIG. 10 illustrates one example 1000 of the BPM 1010 in more detail. The BPM 1010 permits a plethora of calibrated sensor data (digital bridge sense value computed by the computing device 1011) 1012 to be stored in a memory device 1013 and processed by a selection process 1014 (typically under the control of the computing device 1011) and then presented on a visual display device 1015. The selection process 1014 may optionally incorporate a human interface to permit the definition of the selection criterion 1016. One skilled in the art will recognize that a wide variety of selection methodologies may be implemented in the selection process 1014, including but not limited to mean, maximum, minimum, weighted average, range, percent change over time, average absolute deviation, coefficient of variation, interquartile range, percentile, standard deviation, variance, and other methodologies.

In another example, the BPM 1010 permits a plethora of calibrated sensor data (digital bridge sense value computed by the computing device 1011) 1012 to be stored in a memory device 1013 and processed by an analysis process 1014 (typically under the control of the computing device 1011) and then presented on a visual display device 1015. The analysis process 1014 may optionally incorporate a human interface to permit the selection of the analysis algorithm(s) 1016 to be applied to the pressure data 1012. One skilled in the art will recognize that a wide variety of signal analysis methodologies may be implemented in the analysis process 1014, including but not limited to averaging, curve fitting, interpolation, extrapolation, peak fitting, peak selection, mean averaging, and other known analysis techniques. It is specifically anticipated that the high-fidelity nature of the digital data 1012 will permit real-time analysis of the pressure waveforms recorded within the memory device 1013.

In another example, the BPM 1010 permits a plethora of calibrated sensor data (digital bridge sense value computed by the computing device 1011) 1012 to be stored in a memory device 1013 and processed by a sampling process 1014 (typically under the control of the computing device 1011) and then presented on a visual display device 1015. The sampling process 1014 may optionally incorporate a human interface to permit the selection of the sampling criterion 1016 to be applied to the pressure data 1012. Note in this example, a timer and/or time stamp data 1017 may be utilized in conjunction with the memory data 1013 to select or sample a portion of a collected data sample within a given sampling period. One skilled in the art will recognize that this timing function may also be integrated within the computing device 1011.

One skilled in the art will recognize that a wide variety of signal sampling methodologies may be implemented in the sampling process 1014, including but not limited to averaging, decimation, interpolation, resampling, aliasing, oversampling, under sampling, quantization, value limiting, noise filtering, and other known sampling techniques. The data reduction, selection, analysis, and sampling techniques illustrated in FIG. 10 may be combined to form hybrid display architectures that integrate these techniques in a wide variety of ways.

While a wide variety of displays may be utilized in the context of the present disclosure, the use of graphical touch screens may be optimal. Additionally, the use of wireless links to smartphones, computer tablets, and other computing devices is also anticipated within the scope of the present disclosure.

Figure 11:
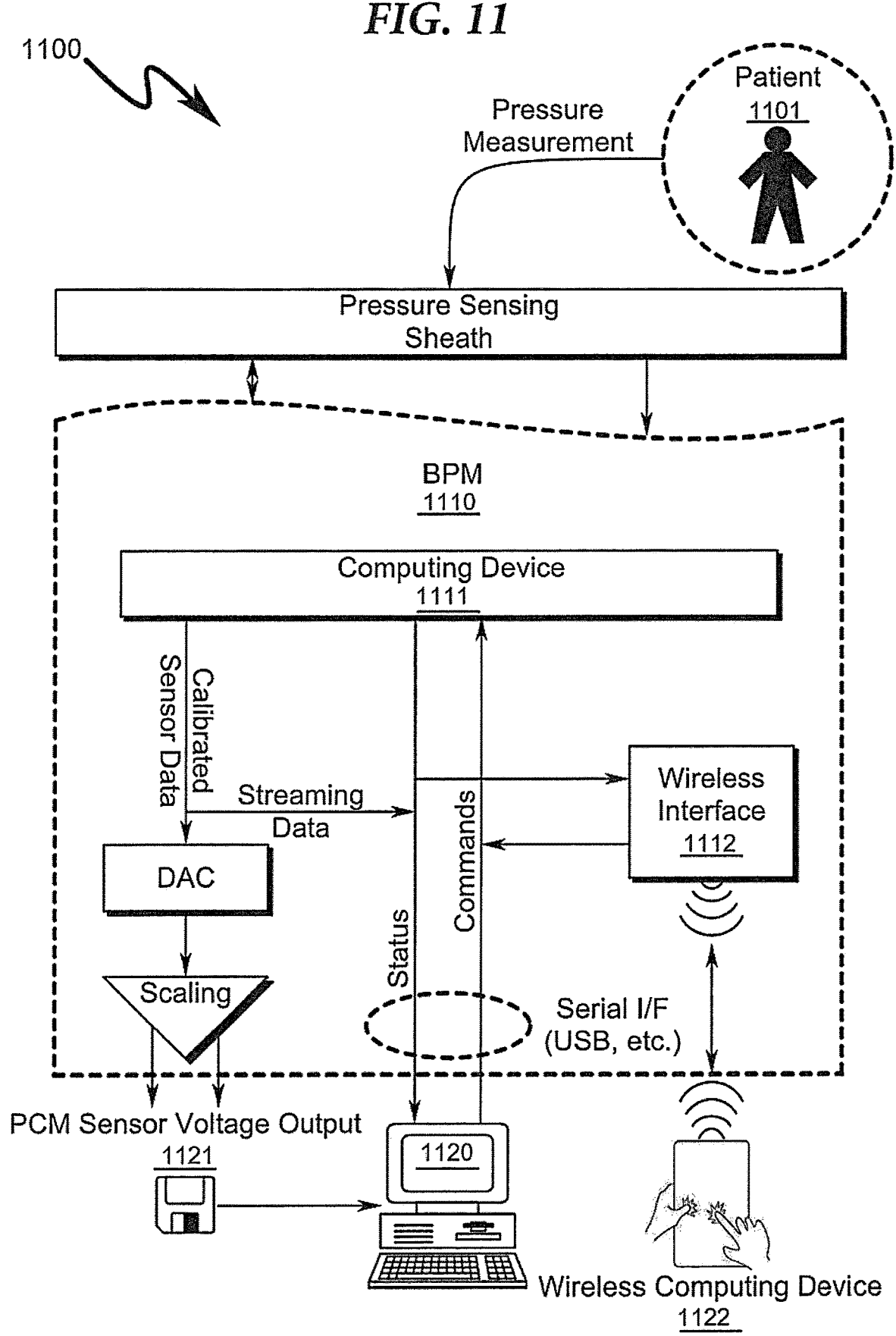
FIG. 11 illustrates an example of the device with a blood pressure monitor (BPM) system that implements bidirectional communication with an external analysis computer using wired and wireless technologies.

FIG. 11 illustrates an example 1100 of a BPM 1110 in which the computing device 1111 may communicate bidirectionally with an external data analysis computer 1120 running under the control of software read from a computer-readable medium 1121. This capability allows for real-time/ offline data/status collection by the analysis computer 1120 and/or configuration/control of the BPM 1110 by the analysis computer 1120.

Within this context it is anticipated that a wireless interface 1112 may be incorporated into the BPM 1110 to permit the use of remote wireless computing devices 1122 (including but not limited to laptops, smartphones, tablet computers, etc.) to function in this data analysis capacity. This wireless interface 1112 may be utilized in some examples of the disclosure where the BPM 1110 is part of a medical device that is embedded within a patient such that pressure measurements are taken continuously (or at specified intervals), and then wirelessly transmitted to a portable display device for storage, analysis, and/or transmission to a physician for further review and diagnosis.

A wide variety of application data collection/analysis software 1121 is envisioned to support patient monitoring and/or diagnosis functions to be performed by either the analysis computing devices 1120, 1122, and/or the computing device 1111 contained within the BPM 1110. On-board real-time and post-processing capability within the computing device 1111 is also anticipated by the present disclosure. This may be implemented using a high-performance processor or multiple processors. Among the potentially valuable functions of this capability include the calculation of fast Fourier transforms, sorting algorithms, searching algorithms, amplitude, power, and phase spectrums, filters, correlations, regressions, confidence intervals, windowing, triggers, thresholding, waveform analysis, wavelet processing, encryption, decryption, formatting, timers, statistical analysis, discrete transform, discrete Fourier transform, time-frequency analysis, etc.

This analysis functionality may be combined with a wide variety of display technologies as anticipated by the present disclosure. This may include a high-resolution graphical display, optionally including touchscreen technology for some applications. This display would be capable of supporting multiple types of graphical readouts (and inputs). The information that could be displayed includes spectral information, amplitude waveforms, filter characteristics, diagnostics, waveform analysis, etc. This capability may directly support the display of sophisticated data analysis detailed above. This capability enables more sophisticated user interaction and simpler user interface development and software updates using soft keys.

The analysis functions detailed above may incorporate a sophisticated internal logging function. In concert with the conventional blood pressure processing applications detailed previously, this logging function tracks and stores information such as sensor performance, environmental exposure, functional monitoring (e.g., power cycles, optics environment, LED life, etc.), software licensing, maintenance periods, compatibility parameters, data quality control, errors, crashes, condition-based maintenance monitoring, PSS insertions, and tracking, etc.

Figure 12:
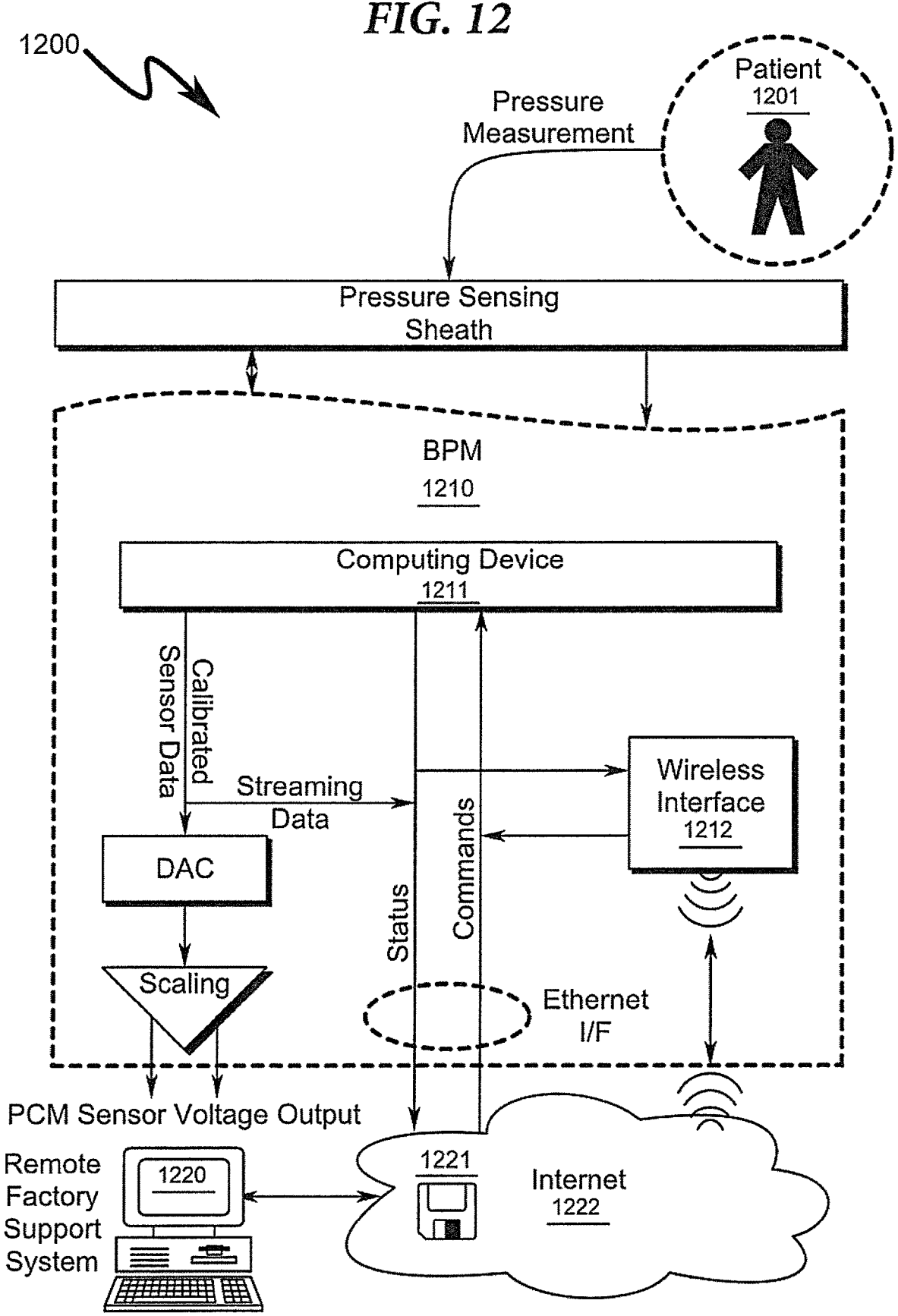
FIG. 12 illustrates an example of the device with a blood pressure monitor (BPM) system that implements bidirectional communication over a computer network for the purposes of providing remote factory support for the BPM.
Figure 13:
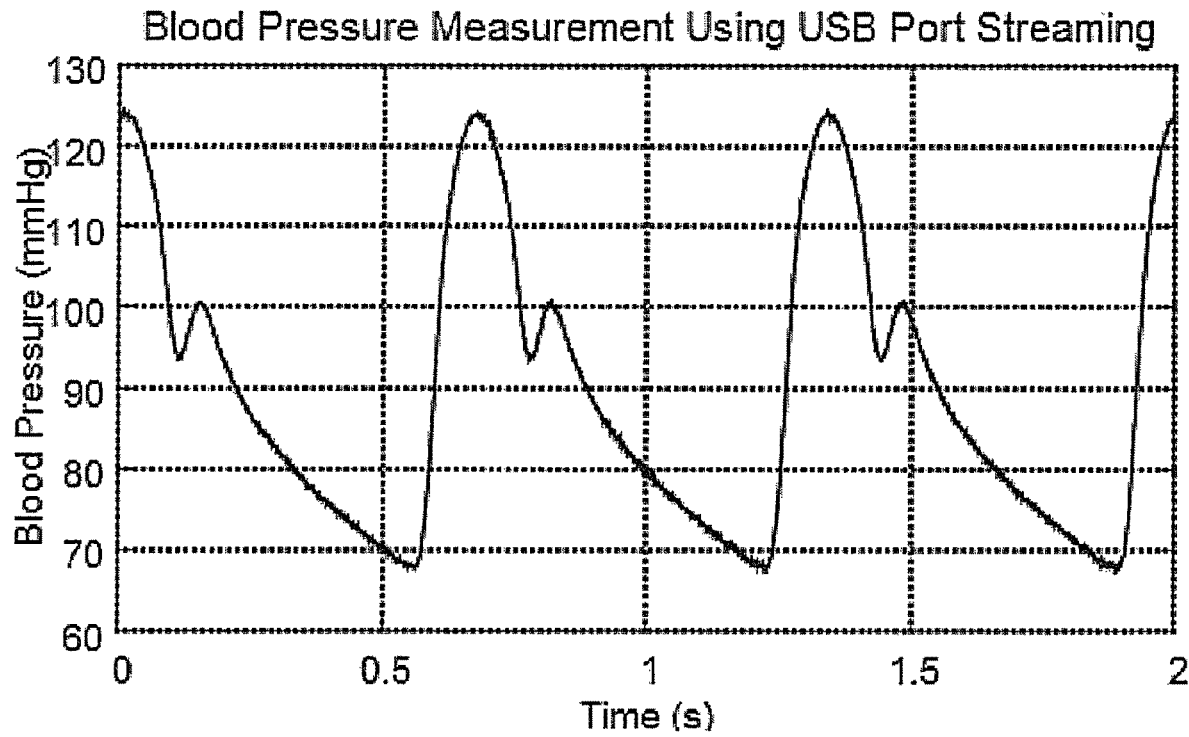
FIG. 13 illustrates an exemplary blood pressure measurement overview result graph obtained via USB data streaming from a preferred exemplary embodiment of the present disclosure.
Figure 14:
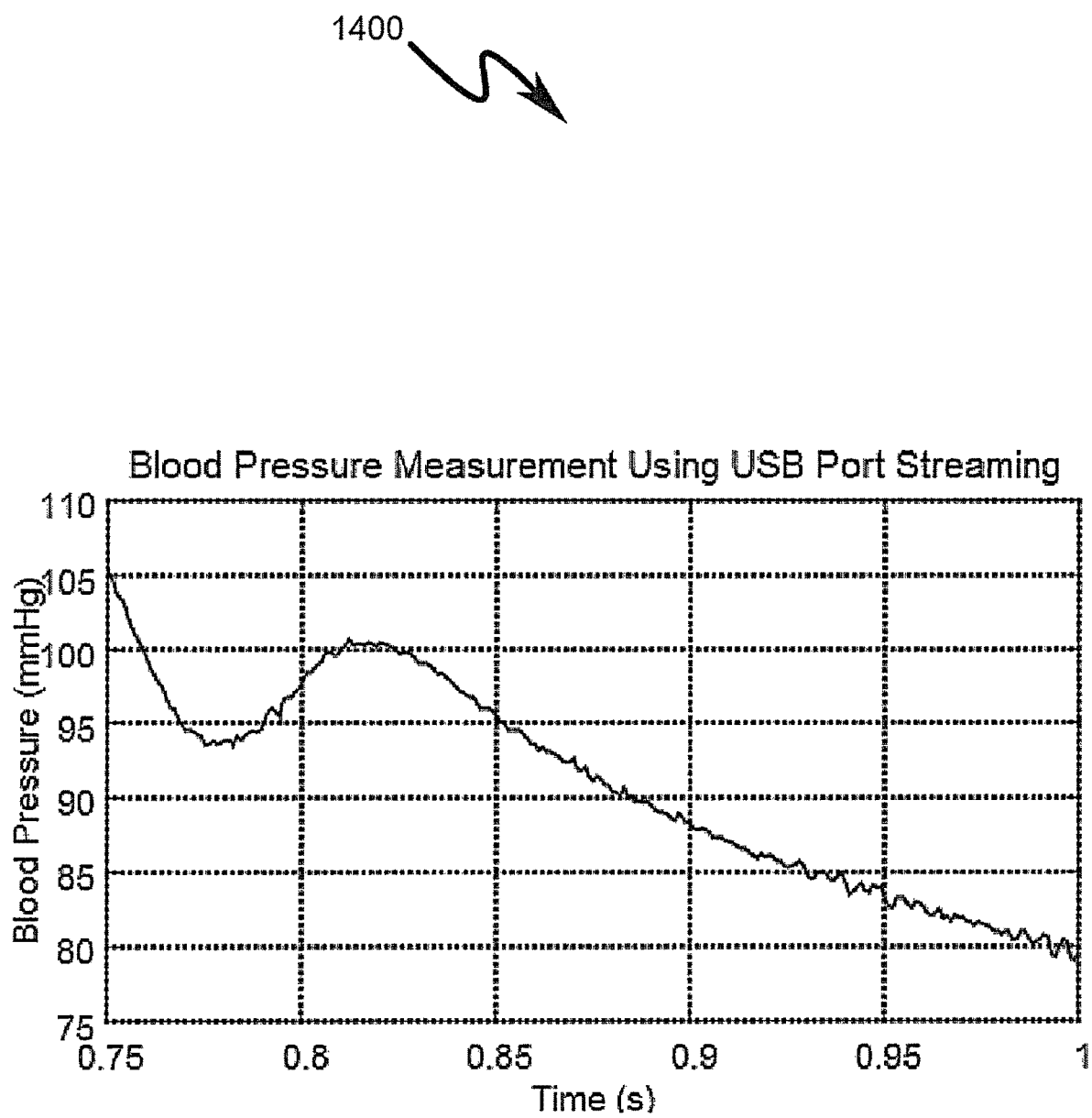
FIG. 14 illustrates an exemplary blood pressure measurement detail result graph obtained via USB data streaming from a preferred exemplary embodiment of the present disclosure.
Figure 15:
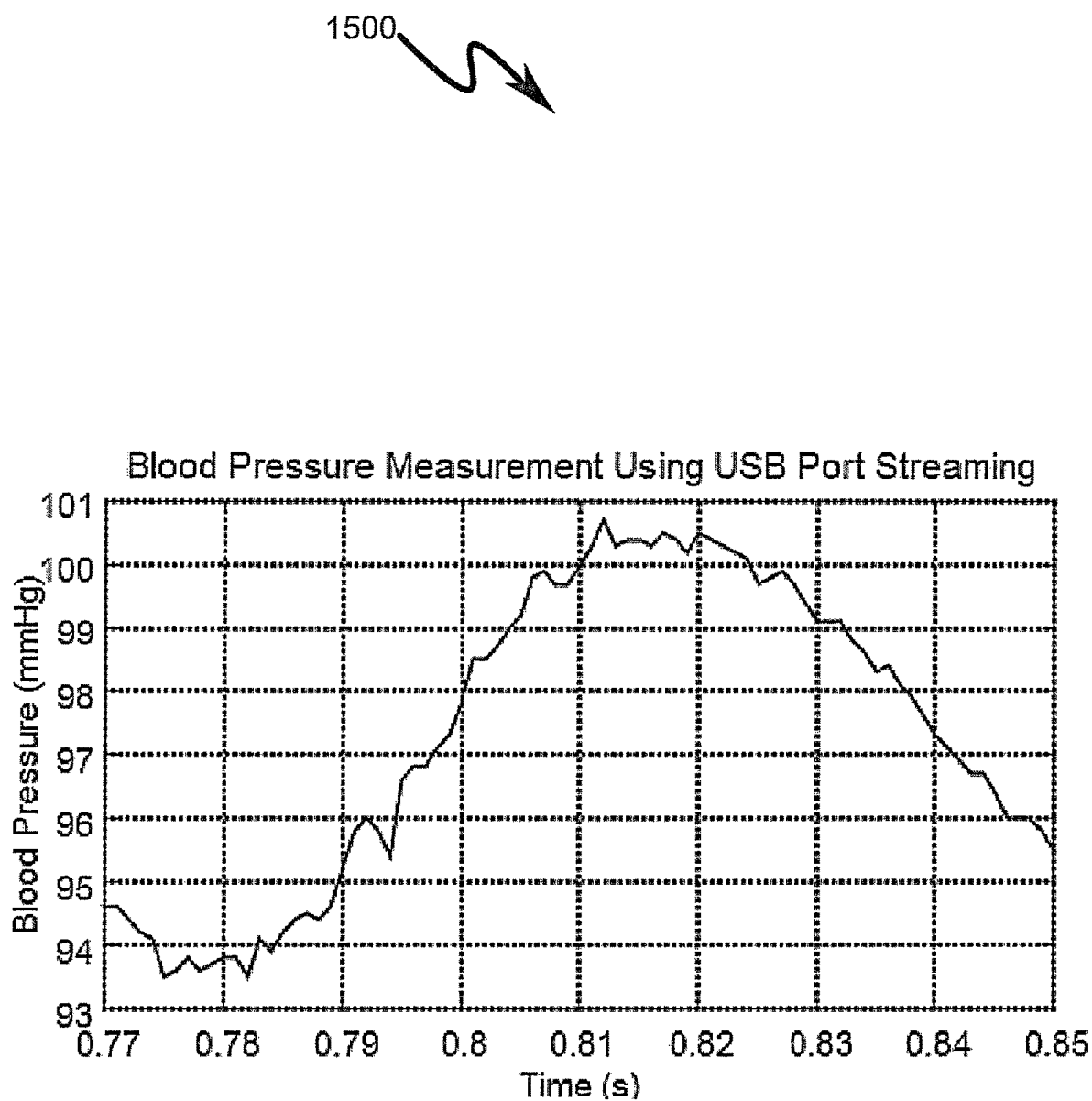
FIG. 15 illustrates an exemplary blood pressure measurement fine detail result graph obtained via USB data streaming from a preferred exemplary embodiment of the present disclosure.
Figure 16:
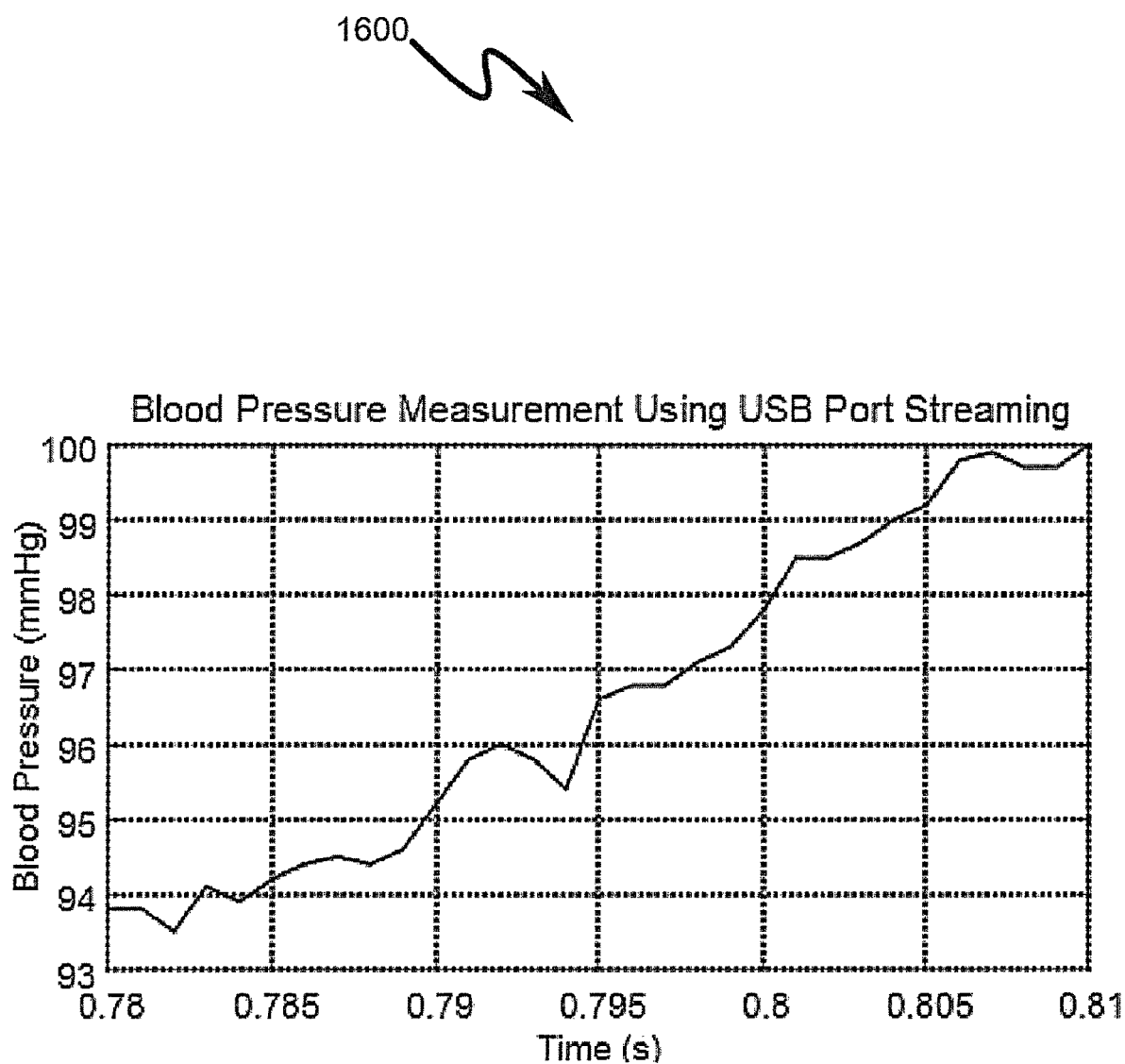
FIG. 16 illustrates an exemplary blood pressure measurement super-fine detail result graph obtained via USB data streaming from a preferred exemplary embodiment of the present disclosure.

FIG. 11 also illustrates that a serial interface (USB, etc.) may be used to communicate between the BPM 1110 and an external computer system for use as a factory maintenance connection. This maintenance functionality may also be field-based, wherein condition-based self-assessment or remote instrument diagnostics and maintenance using wired or wireless connections through the Internet 1222 are implemented as depicted 1200 in FIG. 12. This anticipated capability allows local condition-based as well as factory-level diagnostic and maintenance functions 1220 to be performed remotely in the field, thus reducing costs and downtime. This capability, coupled with the analysis and logging capabilities detailed above, allows the BPM to "call home" when certain conditions occur (outbound device-initiated communication) as well as be accessed by a remote person or application (inbound remotely initiated) to collect information, diagnose problems, devise solutions, download software 1221, and correct problems in the field.

A series of comparison tests were performed on a blood pressure test apparatus to determine BPM conformance to pressure accuracies demonstrated by conventional PCM blood pressure sensors and systems. Static pressure testing comparing a BPM system in comparison to a GE model Dash 3000 conventional PCM blood pressure sensors and systems were performed at a nominal atmospheric pressure of 763.435 mmHg. At least under static pressure measurements, the BPM is in conformance to pressure accuracies demonstrated by conventional PCM blood pressure sensors and systems.

An additional series of comparison tests were performed on a blood pressure test apparatus to demonstrate some of the extremes of pressure at which the present disclosure BPM system continues to register systolic and diastolic pressures, while the conventional PCM blood pressure sensors and system fails to show separation between systolic and diastolic pressures. For this testing, an artificial circulatory system was set up using a beaker of water and a pulsatile pump as the heart. A pressure generator is used to generate an emulated blood pressure waveform under a variety of stroke rates, pulse (heart) rates, systolic pressures, and/or diastolic pressures. A single output port with separate readouts for an external pressure transducer (Wheatstone Bridge) and for a fiber optic output was tested. The testbed permits the direct comparison of traditional PCM-based blood pressure measurements (as displayed on the PCM display) to be compared with both the direct pressure data obtained from the BPM as displayed on the external BPM display, but also how the PCM interprets this raw data as depicted in its Wheatstone Bridge external input display.

The results from this series of comparison tests demonstrate that conventional PCM blood pressure sensors and systems have difficulty in accurately sensing blood pressure from the sensor element under some circumstances. This difficulty extends to external input displays associated with any other analog-based input. There are many factors contributing to errors on the PCM. These errors may include signal dampening from the tubing extending to the Wheatstone Bridge, which is mounted on an IV pole external to the patient, filtration of a signal as it passes to the PCM, or even an algorithmic source of error in how systolic and/or diastolic pressures are calculated. Overall, this testing indicates that while the PCM functions well under ordinary circumstances, it may give erroneous results under extreme circumstances, which are the circumstances where it is most critical that results be error-free. In contrast, the dynamic range of the present disclosure BPM implementation permits accurate measurement operation even under these extreme measurement conditions.

In one example, the BPM is capable of processing 500-1000 blood pressure readings per second. In another example using different sensors, the BPM is capable of processing 250-1000 blood pressure readings per second. These blood pressure readings may be captured in real-time using a digital communications input/output port such as a USB or other serial and/or parallel interface. Examples of data collected using this capture technique using a BioTek pressure waveform simulator are generally illustrated in FIG. 13-16. These waveforms may be analyzed to determine the attributes of the vessel. In some circumstances, these waveforms may be processed in real-time to achieve these same results, permitting physicians to diagnose patient conditions while one or more BPMs are attached to the patient. The BPM described above can be integrated within a variety of blood pressure analysis systems/methods, including but not limited to the following variants.

Figure 17:
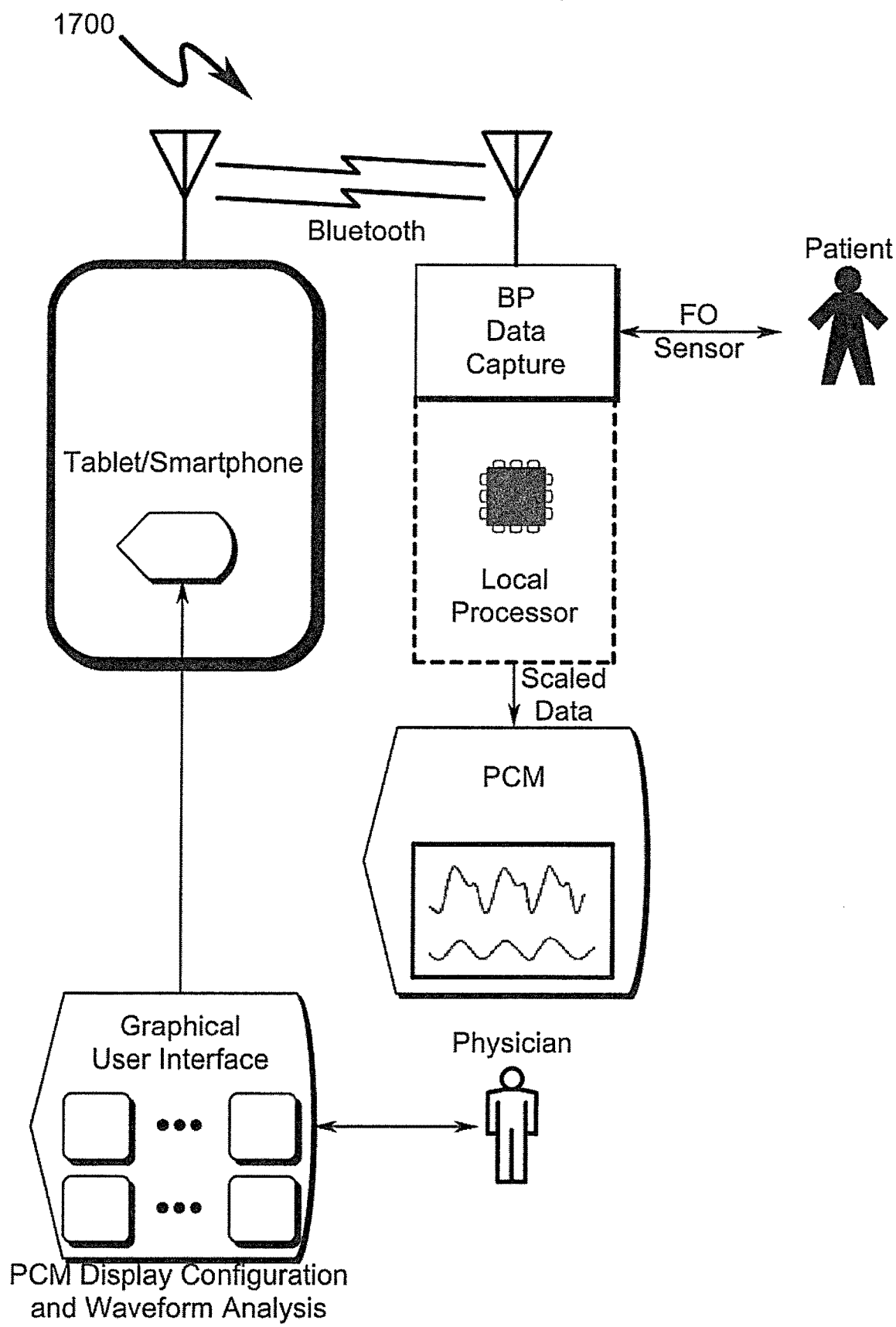
FIG. 17 illustrates an exemplary specialized BPM system architecture.

FIG. 17 illustrates one example of a BPM system, a Specialized BPM System 1700, which capitalizes on the high data capture rate of the BPM system and its ability to capture BP events when the systolic/diastolic pressures approach unity. This capability has targeted applications in neonatal care units as well as trauma centers where the patient's vital signs are often too weak to be accurately captured by conventional PCM systems. In one example, a conventional PCM system is tied to the BP data capture system, which is configured to scale the BP data so that the PCM can accurately display a scaled BP characteristic for the patient. Another option is to permit the display of more accurate BP data on a portable device such as a computer tablet/smartphone. In either case, the faint BP measurements associated with these two classes of patients can be accurately monitored in situations where conventional PCM systems fail to detect any pressure or inaccurately display the pressure.

Figure 18:
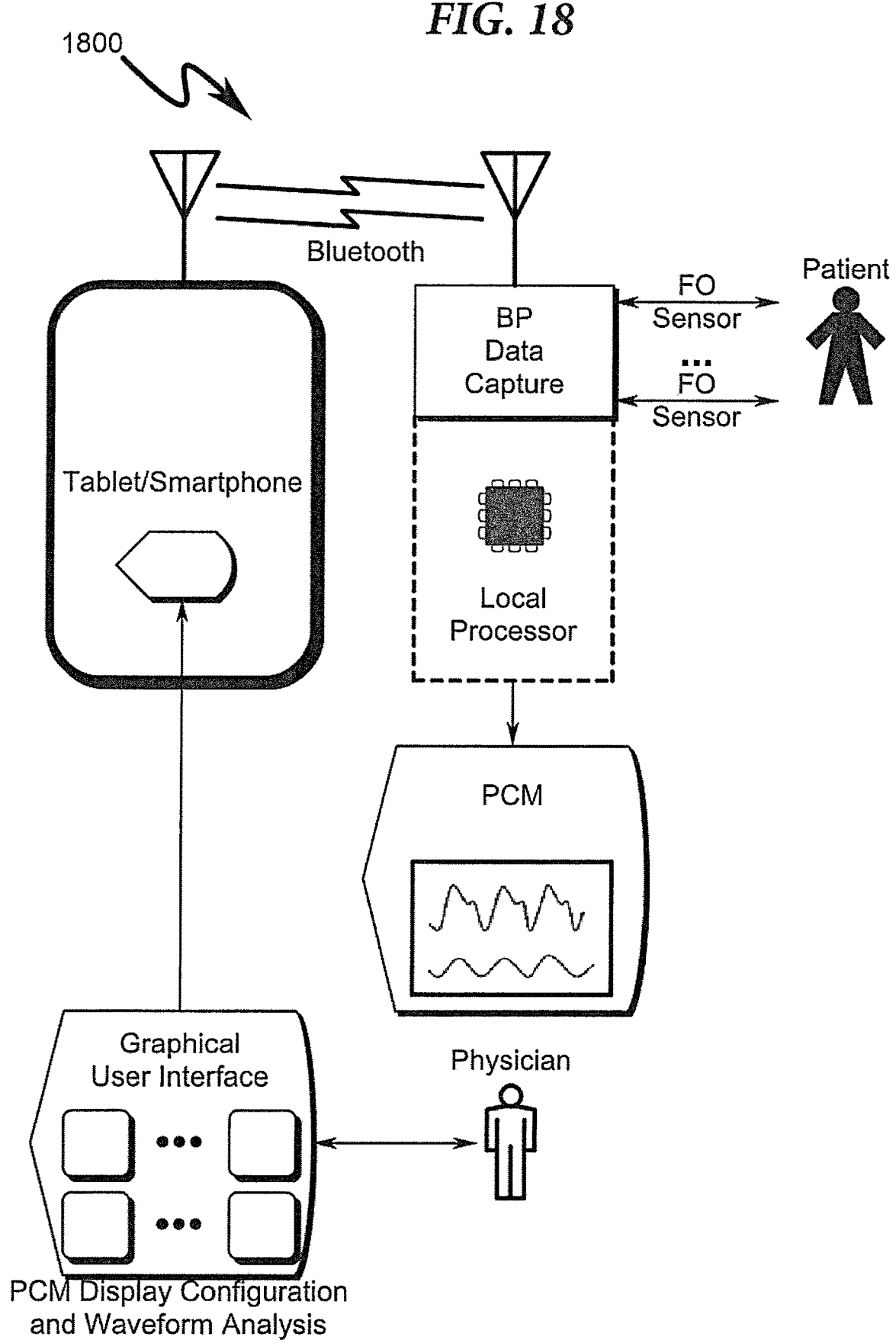
FIG. 18 illustrates an exemplary streaming BP data analysis system architecture.

FIG. 18 illustrates one example of a BPM analysis method, Differential BP sensing 1800, which permits multiple BP sensors placed within a patient to be utilized to measure differential blood pressure readings. For example, this might include pressure sensing surrounding a blood clot or other vascular abnormality or in some cases used to determine blood flow rate in some portion of the patient. In another example, one sensor may be in the arterial system and the other may be in the venous system. The high sensitivity and accuracy of the disclosed BP system permits a range of new patient analysis and diagnosis using these spatially diverse BP sensors which is not possible using conventional PCM BPM technologies available today.

Figure 19:
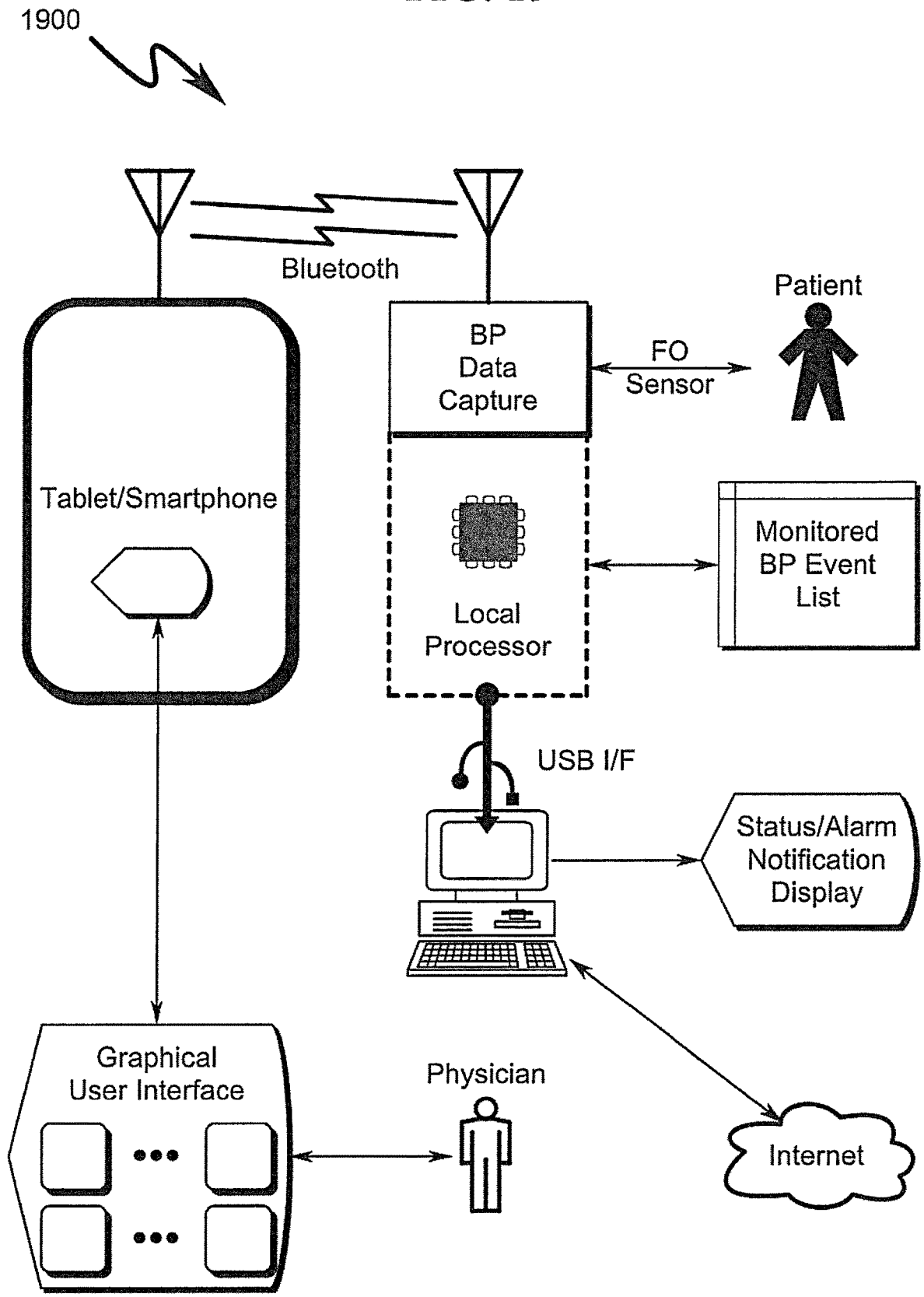
FIG. 19 illustrates an exemplary wireless/remote BPM access system architecture.

FIG. 19 illustrates another example of a BPM analysis method, streaming BP Data Analysis 1900, wherein the USB interface associated with the BPM is used to perform complex analysis of the real-time BP data retrieved from the patient. Since it is not possible to incorporate all the processing/display features desired in an integrated BPM system, the use of a standard PC to perform these analysis functions while streaming real-time BP data from the patient is anticipated. Additional benefits of this approach include the potential to incorporate proactive analysis software to predict potential critical care events for the patient and warn physicians and other healthcare providers of the potential trauma event. This data streaming capability also permits remote diagnosis by other physicians and/or computing systems to be enabled, as well as e-mail/text/pages and other notifications to be generated to remote healthcare professionals if abnormal BP readings are detected in the patient.

Figure 20:
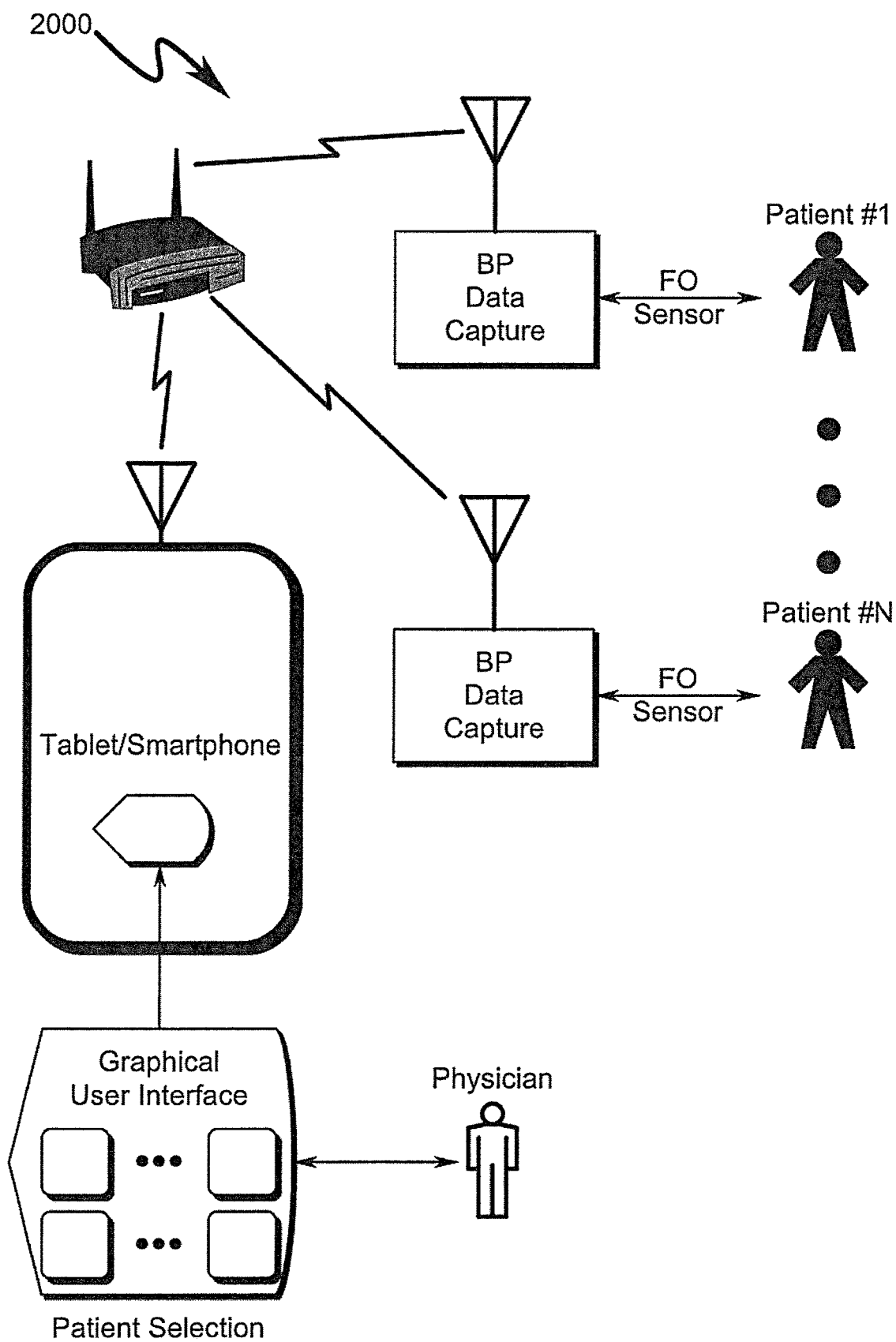
FIG. 20 illustrates an exemplary customized BP analysis system architecture.

FIG. 20 illustrates one example of a BPM access method, streaming Wireless/Remote BPM Access 2000, wherein a physician may access one or more remote BP systems via a portable device such as a tablet/smartphone. The advantage of this approach is that there is no need to have individual PCM systems for each patient, and the physician or other healthcare professional can remotely access the status of any patient via a portable device. This also permits incorporation of sophisticated BP analysis software and other special medical programs within a given portable device, which would not be possible using conventional PCM systems.

Figure 21:
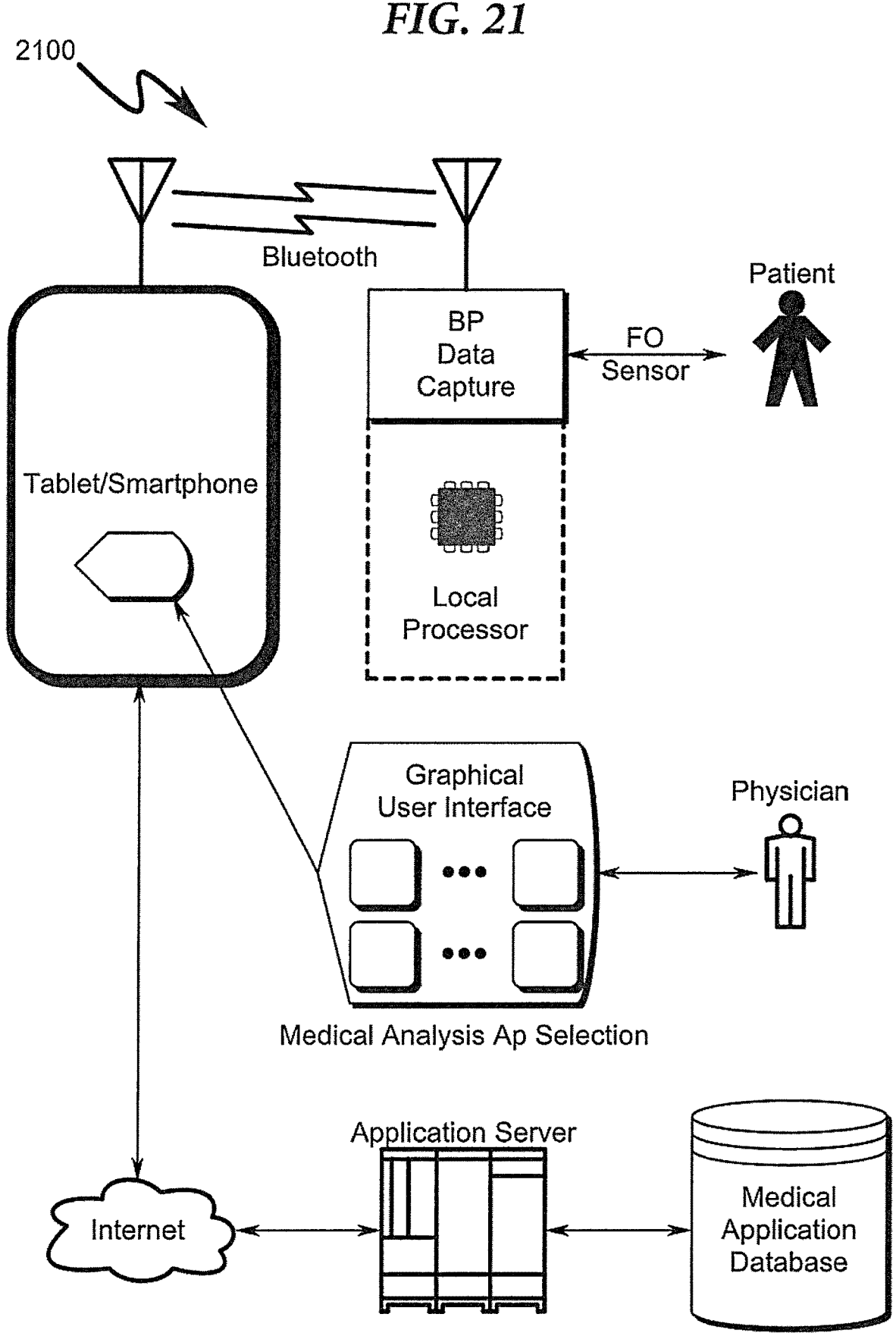
FIG. 21 illustrates one example of the disclosure being utilized in a patient in which one medical device is being advanced through a patient vessel to detect fluid pressure waves within the vessel.

FIG. 21 illustrates another example of a BPM analysis method, customized BP Data Analysis 2100, wherein a physician will interact with the BP data capture system using a wireless interface to a tablet/smartphone. This will allow the physician to select various software applications from a medical application database served over the Internet. These software applications can operate on the tablet/smartphone but may also download software (as application data files) to the local processor associated with the BP data capture device and thus permit real-time analysis of BP readings from the patient.

As previously discussed, the BPM permits a plethora of calibrated sensor data to be stored in a memory device and processed by an analysis process, which may optionally incorporate a human interface to permit selection of the analysis algorithms to be applied to the pressure data. In addition to signal analysis methodologies used to correlate sensor membrane deformation to total fluid pressure in the vessel, the data collected by the sensor can be used to determine specific attributes of the vessel. In one example, the computing device could use the full resolution of the sensor and the fast Fourier transform (FFT) statistical method to provide greater anatomic information and pressure analysis. FFT is a statistical technique that divides a complex waveform into its component sinusoidal waves and assesses the intensity of the component waves. The FFT of a waveform is a complex-valued function representing the component sinusoidal waves. For each frequency, the magnitude of the complex value represents the amplitude of a constituent complex sinusoid with that frequency, and the argument of the complex value represents the complex sinusoid's phase offset. Analytic techniques such as these, as an example, may be used to assess vascular wall stiffness as a component in various diseases, such as atherosclerosis.

By breaking waveforms into component waves, FFT can be used to evaluate differences in waveform activity otherwise undetected when only the combined waveforms are compared. For example, two pressure waves may appear quite similar when only the height of the peaks and the depth of the valleys are considered, but the component waveforms may vary greatly depending on, for example, the elasticity of the walls of the vessel. As an example, a steel tube with fluid waves with a top pressure of 50 mmHg and bottom pressure of 20 mmHg will look the same to a Wheatstone Bridge as a latex tube with the same tops and bottoms. However, they may have very different FFT waves created by the expansion and contraction via the elasticity (or lack thereof) of the walls. Through analysis of these component waveforms, FFT can be used to map, and thus visualize, attributes of a vessel such as elasticity, diameter, and wall thickness. Other statistical analysis methodologies could be used to provide further anatomic information. FFT is a mathematical technique used to evaluate and display sinusoidal waveforms. Cardiac pulsations and arterial waveforms, and hence expansions and contractions in blood vessels and other organs, are sinusoidal, owing to rhythmic contraction and relaxation in the myocardial motion.

A series of tests were performed to demonstrate the value of utilizing FFT to separate pressure waveforms under various conditions despite similar pressures and identify vessel attributes. More specifically, tests were performed to determine whether the use of FFT to analyze high-resolution, high-frequency pressure wave sampling under different vessel conditions enabled differentiation of anatomic circumstances (wall stiffness or stenosis) despite of a lack of clear differentiation based on systolic, diastolic, and mean "arterial" pressures.

A fluidic flow model was created using a pulsatile pump as the heart, a connected tubing system as the vessel, a fluid reservoir to which vessels drained and from which the pump recirculated fluid, and a valve system. Pressure could be titrated via adjustments to the pulse rate and pulse volume on the pump, adjusting the multiple valves in the system, adjustments to the tubing sizes and tubing materials on the inflow and outflow tracts, and changes to the backpressure on the venous system by elevating or lowering the fluid reservoir among the available levels on the table.

The results of this series of tests demonstrates that the use of FFT to analyze pressure wave data under different vessel conditions enables differentiation of vessel attributes despite a lack of clear differentiation based on systolic, diastolic, and mean arterial pressures. While measured systolic, diastolic, and mean arterial pressures were consistent between each type of tubing used in the tests, FFT tracings demonstrates different graphic displays for vinyl tubing, latex tubing, and latex tubing with a stenosis 8 cm long. The FFT tracing for vinyl tubing displayed more numerous, narrower, taller peaks. For latex tubing, the FFT tracing displayed fewer, shorter, and wider peaks. Finally, the FFT tracing for latex tubing with a stenosis displayed a wider peak representing the primary pulsation as the sensor became more distant from the stenosis.

Changes in FFT along the course of a vessel may enable localized interventions. Different diseases may have their own FFT "signature" based on the alterations they produce in the vessel wall dynamics. FFT provides a potential means for visualization of physiologic differences between these parameters with localization prior to development of more grossly evident anatomical interruption. In some embodiments, the FFT statistical analysis may be used to assess cardiovascular integrity from the optical sensor inserted alone or as part of a medical device. For example, Fourier transform may be used to assess cardiovascular integrity using signals from a fiber optic pressure sensor inserted alone, or as part of a medical device, into cardiovascular structure(s) in the body. In other embodiments, the FFT statistical analysis may be used to assess CSF or brain pressures from the optical sensor inserted alone or as part of another medical device. For example, Fourier transform may be used to assess CSF or brain pressures by inserting a pressure sensor, either alone or as part of another medical device, into a brain or spinal subarachnoid space.

Figure 22:
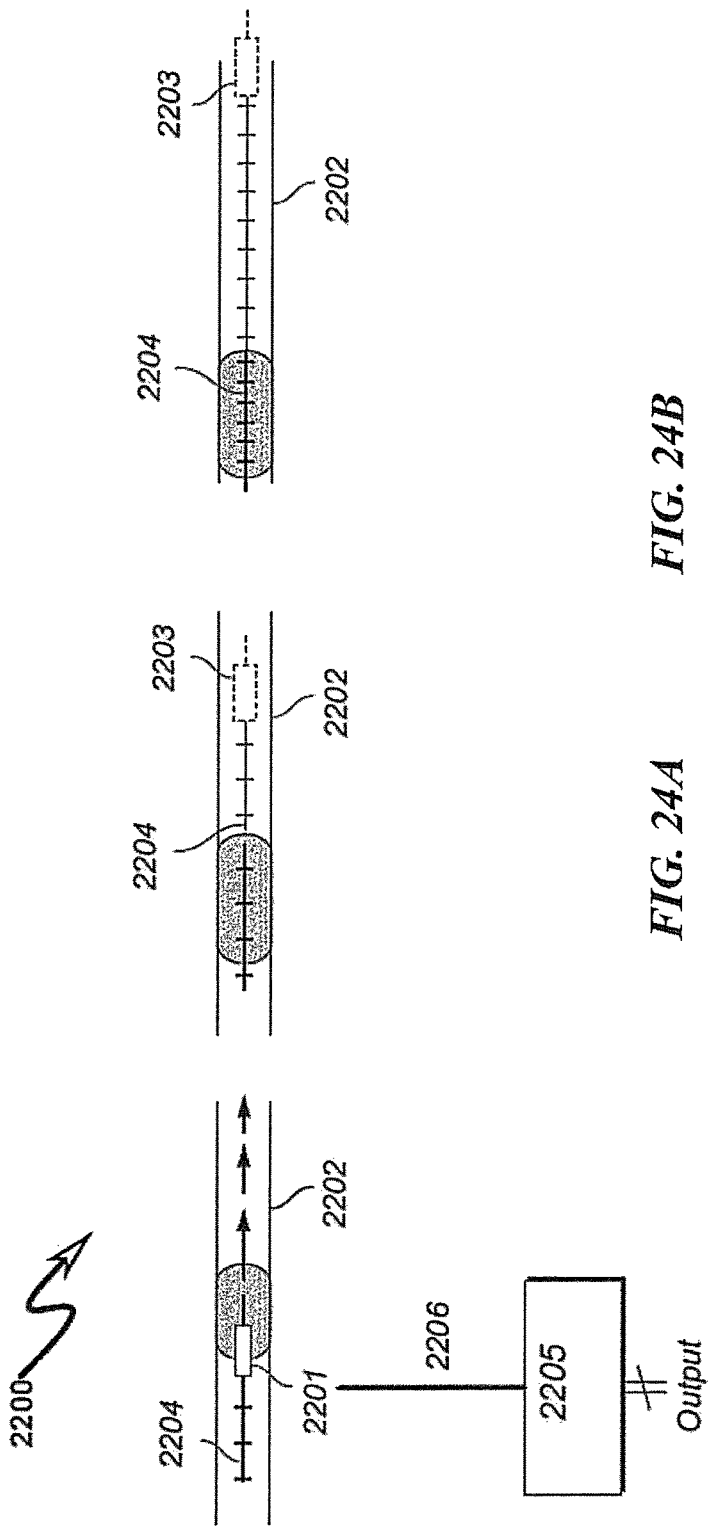
FIG. 22 illustrates one example of the disclosure being utilized in the patient in which two medical devices are used to detect fluid pressure wave differences between the two devices.

FIG. 22 illustrates one example of the disclosure being utilized in a patient 2200. In at least one example, one medical device 2201 could be inserted into a patient vessel 2202 at a point in the patient's body. The specific point at which a medical device 2201 is inserted in the patient vessel 2202 depends on where the user intends to measure the patient's blood pressure waves. In this example, a medical device 2201 would be advanced 2203 through the vessel 2202. As a medical device 2201 is moved through the vessel 2203, a measurement device 2204 would provide information regarding the location of a medical device 2201 within the vessel 2202 and a fiber optic sensor would detect fluid pressure within the vessel 2202. Output from a sensor would be processed by a signal conditioner. As previously described, a medical device 2201 is coupled to a BPM 2205 via a cable 2206 Output from a signal conditioner would be received by a BPM 2205. Using FFT, the computing device could transform pressure wave data to provide information regarding the attributes of the segment of the vessel 2202 traversed (2203) by the medical device 2201.

Figure 23:
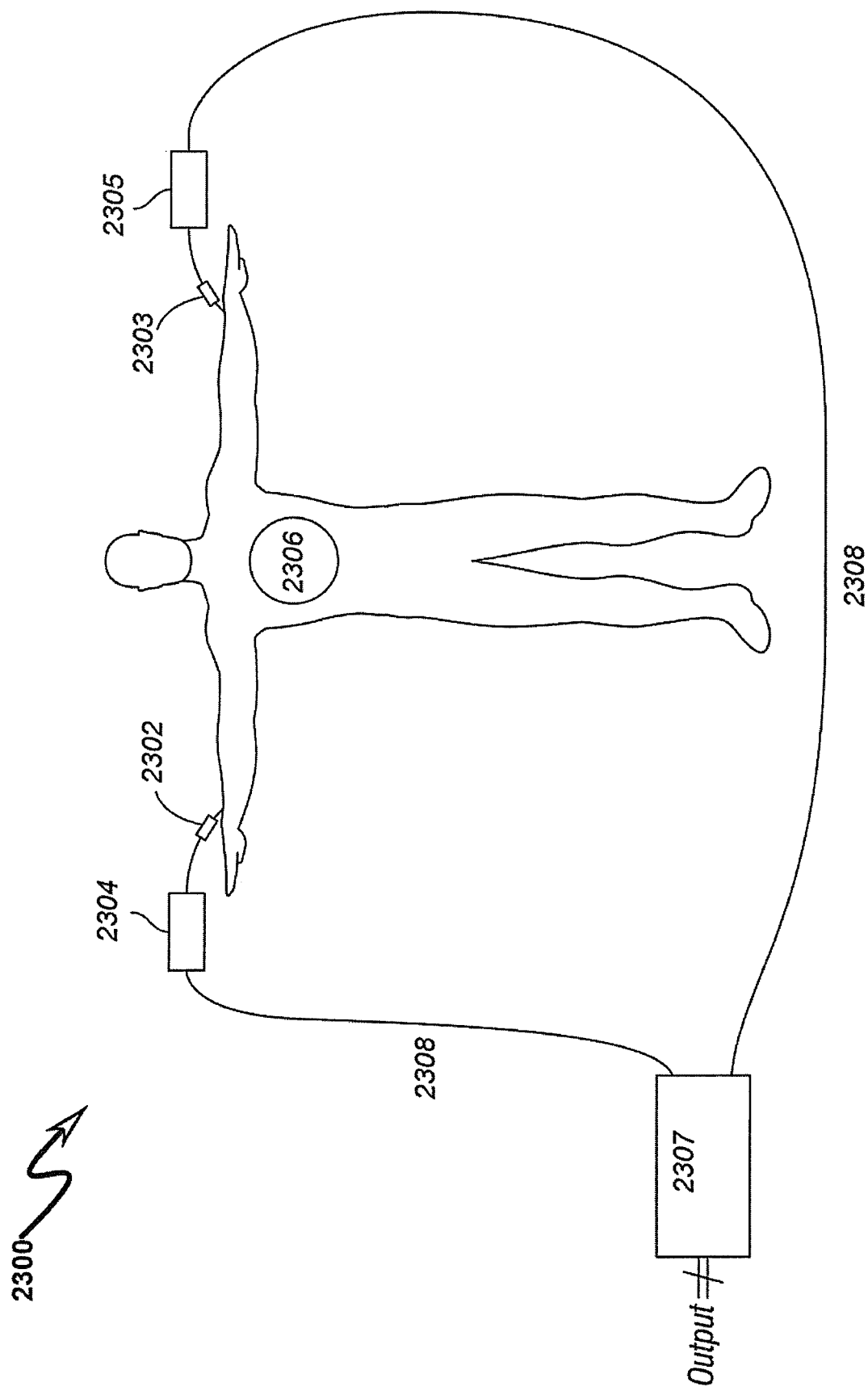
FIG. 23 illustrates one example of the disclosure being utilized in a patient.

FIG. 23 illustrates one example of the disclosure being utilized in a patient. In at least one example 2300, two medical devices 2302 and 2303 could be inserted into a patient 2301 at opposite ends of a vessel. Measurement devices 2304, 2305 would provide information regarding the location of each medical device 2302, 2303, respectively, within the vessel. The medical devices 2303, 2303 would remain stationary while the fiber optic sensors detect fluid pressure from different points within the vessel. The sensor 2302 at the proximal end of the vessel would detect pressure changes caused by the contraction of the heart muscle 2306. Alternatively, the proximally placed sensor 2302 could be used to detect pressure changes caused by other types of pumps. The sensor 2303 at the distal end of the vessel would detect a second pressure wave, which would include components produced by vessel attributes between the distal sensor 2303 and proximal sensor 2302. As previously described, the medical devices 2302, 2303 are coupled to a BPM 2307 via cables 2308. Output from each signal conditioner would be received by a BPM 2307. Using FFT, the computing device could transform pressure wave data to provide information regarding the attributes of the segment of the vessel traversed by the medical devices 2302, 2303. In this example, the computing device would perform further analysis to compare FFT output from each device 2302, 2303 to provide information regarding the attributes of the vessel between the two devices 2302, 2303. While FFT was described in these examples, it would be understood that other forms of transforms, such as Laplace or Z transforms, or others like them, along with statistical analysis, could provide outputs that would be useful for these types of analysis.

Figure 24B:
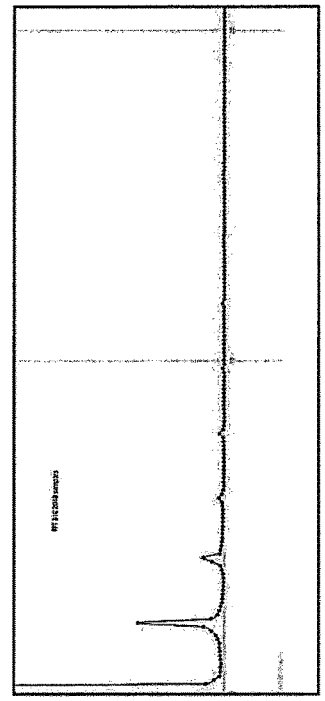
FIGS. 24A & FIG. 24B illustrate two waveforms created using FFT analysis from readings taken from an optical sensor placed in different locations on the same test subject.
Figure 24A:
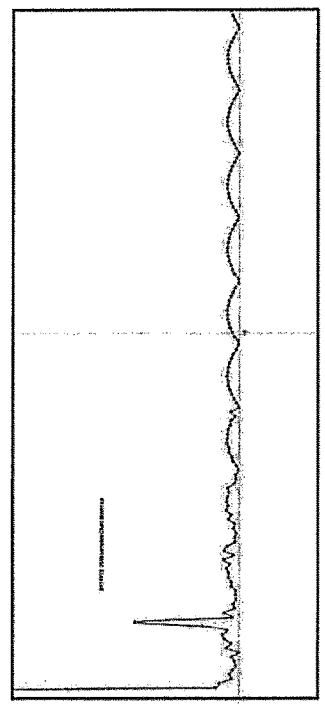

Turning now to FIG. 24A and FIG. 24B, illustrated are two waveforms created using FFT analysis from readings taken from an optical sensor placed in different locations on the same test subject. FIG. 24A illustrates the FFT reading from an optical sensor placed in the heart (the left ventricle) of the subject, and FIG. 24B illustrates the FFT reading from an optical sensor placed in the aorta above the aortic valve. The two illustrated FFT waveforms were obtained within a couple of minutes of each other, and therefore the blood pressures were quite similar within the same test subject. Thus, the minor difference between these FFT waveforms is caused by anatomic differences between the two locations of the two optical sensors, but as illustrated, the overall similarities of the waveforms demonstrate the accuracy provided by the systems, devices, and methods of the disclosed principles.

The present disclosure may include a computing device that can include any of an application specific integrated circuit (ASIC), a microprocessor, a microcontroller, a digital signal processor (DSP), a field-programmable gate array (FPGA), or equivalent discrete or integrated logic circuitry. In some examples, the system may include multiple components, such as any combination of one or more microprocessors, one or more microcontrollers, one or more DSPs, one or more ASICs, or one or more FPGAs. It would also be understood that multiples of the circuits, processors, or controllers could be used in combination or in tandem, or multithreading. Additionally, it would be understood that a browser or program could be implemented on a mobile device or mobile computing device, such as, a phone, a mobile phone, a cell phone, a tablet, a laptop, a mobile computer, a personal digital assistant ("PDA"), a processor, a microprocessor, a micro controller, or other devices or electronic systems capable of connecting to a user interface and/or display system. A mobile computing device or mobile device may also operate on or in the same manner as the computing device disclosed herein or be based on improvements thereof. Outputs of results from the device(s) may be transmitted wirelessly (e.g., Bluetooth) from the point of collection of data (sensors) to a remote location for analysis.

The components of the present disclosure may include any discrete and/or integrated electronic circuit components that implement analog and/or digital circuits capable of producing the functions attributed to the modules herein. For example, the components may include analog circuits, e.g., amplification circuits, filtering circuits, and/or other signal conditioning circuits. The components may also include digital circuits, e.g., combinational or sequential logic circuits, memory devices, etc. Furthermore, the modules may comprise memory that may include computer-readable instructions that, when executed cause the modules to perform various functions attributed to the modules herein.

Memory may include any volatile, non-volatile, magnetic, or electrical media, such as a random-access memory (RAM), dynamic random-access memory (DRAM), static random-access memory (SRAM), read-only memory (ROM), non-volatile RAM (NVRAM), electrically-erasable programmable ROM (EEPROM), flash memory, hard disks, or any other digital media. Additionally, there may also be a tangible non-transitory computer readable medium that contains machine instructions, such as, a (portable or internally installed) hard drive disc, a flash drive, a compact disc, a DVD, a zip drive, a floppy disc, optical medium, magnetic medium, or any other number of possible drives or discs, that are executed by the internal logic of a computing device. It would be understood that the tangible non-transitory computer readable medium could also be considered a form of memory or storage media.

While this disclosure has been particularly shown and described with reference to preferred embodiments, it will be understood by those skilled in the art that various changes in form and detail may be made therein without departing from the spirit and scope of the invention. The inventors expect skilled artisans to employ such variations as appropriate, and the inventors intend the invention to be practiced otherwise than as specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

While various embodiments in accordance with the principles disclosed herein have been described above, it should be understood that they have been presented by way of example only, and not limitation. Thus, the breadth and scope of this disclosure should not be limited by any of the above-described exemplary embodiments, but should be defined only in accordance with any claims and their equivalents issuing from this disclosure. Furthermore, the above advantages and features are provided in described embodiments, but shall not limit the application of such issued claims to processes and structures accomplishing any or all of the above advantages.

Additionally, the section headings herein are provided for consistency with the suggestions under 37 C.F.R. 1.77 or otherwise to provide organizational cues. These headings shall not limit or characterize the invention(s) set out in any claims that may issue from this disclosure. Specifically, and by way of example, although the headings refer to a "Technical Field," the claims should not be limited by the language chosen under this heading to describe the so-called field. Further, a description of a technology as background information is not to be construed as an admission that certain technology is prior art to any embodiment(s) in this disclosure. Neither is the "Brief Summary" to be considered as a characterization of the embodiment(s) set forth in issued claims. Furthermore, any reference in this disclosure to "invention" in the singular should not be used to argue that there is only a single point of novelty in this disclosure. Multiple embodiments may be set forth according to the limitations of the multiple claims issuing from this disclosure, and such claims accordingly define the embodiment(s), and their equivalents, that are protected thereby. In all instances, the scope of such claims shall be considered on their own merits in light of this disclosure, but should not be constrained by the headings set forth herein.

What is claimed is:

1. A device for measuring internal blood pressure and mapping an internal surface of a vessel carrying a fluid, the device comprising:
   (a) an optical sensor emitting light of a known wavelength and capturing light reflected from the emitted light, the sensor located in a housing having a deformable membrane, wherein the emitted light reflects off of the membrane;
   (b) a signal conditioner processing detection of the reflected light to generate electrical signals proportional to corresponding amounts of deformation of the membrane caused by pressure changes in the vessel deforming the membrane;
   (c) a computing device calculating pressure readings in the vessel by correlating corresponding amounts of deformation to a total fluid pressure in the vessel using the electrical signals; and
   (d) a memory for storing a plurality of pressure readings calculated at regular intervals, wherein the computing device further correlates membrane deformation to pressure wave information and determines vessel attributes following statistical analysis of pressure changes among the plurality of pressure readings.

2. The device of claim 1, wherein the total fluid pressure within the vessel includes a first pressure component produced by a heart muscle and a second pressure component from a vessel attribute.

3. The device of claim 2, wherein the computing device correlating the amount of deformation to a total fluid pressure in the vessel comprises subtracting the first pressure component from the calculated total pressure.

4. The device of claim 1, wherein the computing device performs a zero calibration function prior to the correlating.

5. The device of claim 1, wherein the computing device analyzes pressure wave data using methods of statistical analysis including Fast Fourier transformation (FFT).

6. The device of claim 5, wherein the FFT statistical analysis assesses cardiovascular integrity from the optical sensor inserted alone, or as part of a medical device, into a cardiovascular structure.

7. The device of claim 5, wherein the FFT statistical analysis assesses CSF or brain pressures from the optical sensor inserted alone, or as part of another medical device, into a brain or spinal subarachnoid space.

8. The device of claim 1, further comprising a bridge emulator and a bridge excitation converter, wherein the bridge excitation converter generates a scaling reference signal for use by the bridge emulator to provide compensated analog bridge sense signals representing corresponding compensated and calibrated conversions of the electrical signals.

9. The device of claim 8, further comprising a bridge sense D/A converter, wherein the bridge sense D/A converter received the scaling reference signal and generates the compensated analog bridge sense signals.

10. A method for measuring internal blood pressure and mapping an internal surface of a vessel carrying a fluid, the method comprising:
    (a) locating an optical sensor in a housing having a deformable membrane;
    (b) emitting, using the optical sensor, light of a known wavelength;
    (c) capturing, using the optical sensor, light reflected from the emitted light reflecting off of the membrane;
    (d) processing, using a signal conditioner in communication with the optical sensor, detection of the reflected light to generate electrical signals proportional to corresponding amounts of deformation of the membrane caused by pressure changes in the vessel deforming the membrane;
    (e) calculating, using a computing device, pressure readings in the vessel by correlating corresponding amounts of deformation to a total fluid pressure in the vessel using the electrical signals;
    (f) storing, in a memory, a plurality of pressure readings calculated at regular intervals; and
    (g) correlating, with the computing device, membrane deformation to pressure wave information to determine vessel attributes following statistical analysis of pressure changes among the plurality of pressure readings.

11. The method of claim 10, wherein the total fluid pressure within the vessel includes a first pressure component produced by a heart muscle and a second pressure component from a vessel attribute.

12. The method of claim 11, wherein correlating, with the computing device, the amount of deformation to a total fluid pressure in the vessel comprises subtracting the first pressure component from the calculated total pressure.

13. The method of claim 10, further comprising performing, with the computing device, a zero calibration function prior to the correlating.

14. The method of claim 10, further comprising analyzing, with the computing device, pressure wave data using methods of statistical analysis including Fast Fourier transformation (FFT).

15. The method of claim 14, wherein the FFT statistical analysis assesses cardiovascular integrity from the optical sensor inserted alone, or as part of a medical device, into a cardiovascular structure.

16. The method of claim 14, wherein the FFT statistical analysis assesses CSF or brain pressures from the optical sensor inserted alone, or as part of another medical device, into a brain or spinal subarachnoid space.

17. The method of claim 10, further comprising generating, using a bridge excitation converter, a scaling reference signal for use by a bridge emulator to provide compensated analog bridge sense signals representing corresponding compensated and calibrated conversions of the electrical signals.

18. The method of claim 17, further comprising receiving, using a bridge sense D/A converter, the scaling reference signal to generate the compensated analog bridge sense signals.

* * * * *